United States Patent [19]

Katoh et al.

[11] Patent Number: 5,169,749
[45] Date of Patent: Dec. 8, 1992

[54] PHOTOGRAPHIC MATERIALS WITH COUPLERS CONTAINING PROTECTED FORMYL GROUPS

[75] Inventors: Eisaku Katoh; Shuji Kida; Shuichi Sugita, all of Hino, Japan

[73] Assignee: Konica Corporation, Tokyo, Japan

[21] Appl. No.: 686,499

[22] Filed: Apr. 17, 1991

[30] Foreign Application Priority Data

Apr. 19, 1990 [JP] Japan .................... 2-103635
Dec. 26, 1990 [JP] Japan .................... 2-414013

[51] Int. Cl.$^5$ ............ G03C 7/32; G03C 7/34; G03C 7/36; G03C 7/38
[52] U.S. Cl. ............ 430/548; 430/226; 430/359; 430/543; 430/553; 430/555; 430/557
[58] Field of Search ............ 430/359, 226, 543, 548, 430/553, 555, 557

[56] References Cited

U.S. PATENT DOCUMENTS 4,749,644 6/1988 Tosaka et al. .............. 430/544
4,777,120 11/1988 Lau ............................. 430/359

FOREIGN PATENT DOCUMENTS 0313308  4/1989  European Pat. Off. .
3621561A1 1/1987  Fed. Rep. of Germany .
59-28745  2/1984  Japan .
59-195234 11/1984 Japan .
62-200349 9/1987  Japan .
62-204257 9/1987  Japan .
1-134454  5/1989  Japan .

OTHER PUBLICATIONS

Patent Abstracts of Japan, vol. 11, No. 386 (P-647)[2833]Dec. 17, 1987.

*Primary Examiner*—Richard L. Schilling
*Attorney, Agent, or Firm*—Finnegan, Henderson, Farabow, Garrett and Dunner

[57] ABSTRACT

The improved silver halide photographic material has a substantially colorless coupler that has a leaving group with a protected formyl group at the active site, said protected formyl group being such that subsequent to the elimination of the leaving group upon coupling reaction, the protective group for a formyl group undergoes cleavage, causing reaction with an aromatic primary amine to form a ballasted Schiff type dye. The novel substantially colorless coupler is capable of highly efficient dye formation.

10 Claims, No Drawings

PHOTOGRAPHIC MATERIALS WITH COUPLERS CONTAINING PROTECTED FORMYL GROUPS

BACKGROUND OF THE INVENTION

This invention relates to silver halide photographic materials containing novel couplers.

The recent improvement in the quality of image achievable with silver halide color photographic materials has been remarkable but not so in terms of their sharpness quality. One important means for providing improved sharpness is to reduce the thickness of the coating structure. Particularly in the case of a silver halide emulsion layer that is closer to the support of a multilayer coating, the optical path of the scattering of light incident on the surface of the light-sensitive material is long and it is largely for this reason that making that emulsion layer as thin as possible by reducing its binder content is held to be an effective means for providing improved sharpness. Conventionally known methods for reducing the thickness of emulsion layers are based on reducing the oil or gelatin content by using polymer couplers as taught in Unexamined Published Japanese Patent Application No. 28745/1984 or low-molecular weight couplers capable of efficient color formation as taught in Unexamined Published Japanese Patent Application No. 195234/1984. However, none of these techniques have been found to satisfy the need for efficient color formation or desilvering during processing. Unexamined Published Japanese Patent Application Nos. 200349/1987, 204257/1987 and 134454/1989 teach the use of couplers that have as a coupling-off group a dye whose maximum spectral absorption is shifted temporarily to shorter wavelength by blocking an auxochrome. Upon reaction with the oxidation product of a developing agent, such couplers form another molecule of dye in addition to the azomethine dye formed from ordinary couplers. These "one-equivalent couplers" are significantly improved in the efficiency of color formation over conventional couplers but the spectral absorption of the dye combined with these couplers is not shifted to sufficiently shorter wavelength so that the couplers per se will absorb visible light to cause unwanted phenomena such as desensitization.

Further, these couplers are colored and modes of their utility are limited. For example, they are not suitable for use in reversal films, color papers and other light-sensitive materials intended for direct viewing.

SUMMARY OF THE INVENTION

The present invention has been achieved under these circumstances and has as an object providing silver halide photographic materials that contain novel colorless couplers that achieve highly efficient color formation.

This object of the present invention can be attained by a silver halide photographic material that contains a substantially colorless coupler, which coupler has a coupler residue and a leaving group having a protected formyl group.

DETAILED DESCRIPTION OF THE INVENTION

The novel coupler to be used in the present invention has a coupler residue and a leaving group with a protected formyl group at the active site. The protected formyl group is such that subsequent to the elimination of the leaving group upon coupling reaction, the protective group for a formyl group undergoes cleavage, causing reaction with an aromatic primary amine to form a non-diffusible Schiff type dye.

The leaving group eliminated from the coupler upon coupling reaction reacts with the yet to be oxidized color developing agent, with the protective group being cleaved, thereby producing a dye without involving a redox reaction.

The term "protected formyl group" means a group that is produced by reacting a formyl group with a group capable of protecting said formyl group and which reverts to the formyl group upon hydrolysis. The protected formyl group may be of any type that experiences a reaction for deprotection when or after the leaving group is released from the coupler. Exemplary protective groups are described in Green, "Protective Groups in Organic Synthesis", John Wiley & Sons, pp. 114–151, 1980. Preferred examples of the protected formyl group include groups of acetal type, hemithioacetal type, dithioacetal type, N,N-acetal type and N,O-acetal type.

The dye to be produced from the leaving group is preferably a non-diffusible dye.

An example of the novel coupler to be used in the present invention may be represented by the following general formula (I):

$$Cp-(L)_n-A \qquad (I)$$

where Cp is a coupler residue excluding the hydrogen atom at the active site; L is a linkage group; n is an integer of 0 or 1, provided that n being zero means direct attachment of A to Cp; and A is an organic group having a protected formyl group.

The coupler residue Cp is known and may be selected from among various kinds without particular limitation. For example, it may be a coupler residue that generates a chromatic dye upon reaction with the oxidation product of a developing agent. Alternatively, Cp may be a coupler residue that does not form a chromatic dye. The coupler of the general formula (I) can be used as a one-equivalent coupler if it is so designed that the dye to be formed by reaction between A released from Cp and the developing agent will have the same color as the dye to be generated from Cp. From the viewpoints of such factors as spectral absorption characteristics and image keeping quality, it is also possible to utilize only the dye that is generated from the portion released from the coupler residue Cp and, in this case, coupler residues that generate substantially colorless compounds upon reaction with the oxidation product of a developing agent or those which dissolve away into the developing solution after generating chromatic compounds may be used.

The dye to generated by the reaction between A and a developing agent is preferably designed to have a color that corresponds to the spectral absorption wavelength of the dye to be generated by the reaction between the coupler residue and the oxidation product of the developing agent. However, the color of the former dye may be varied depending on a specific use. For instance, in order to correct the spectral absorption of the dye to be generated from the coupler residue, a dye may be generated by reaction between A and the developing agent in such a way that its maximum spectral absorption is shifted towards slightly longer or shorter wavelength. If necessary, a dye having an entirely different color may be generated.

The general formula (I) is described below in greater detail.

Examples of the coupler residue Cp that generate chromatic dyes include yellow coupler residues, magenta coupler residues, cyan coupler residues and other coupler residues that are used in known customary dye-forming couplers which form colored products upon reaction with oxidized developing agents.

Typical examples of the yellow coupler residue represented by Cp are described in U.S. Pat. Nos. 2,298,443, 2,407,210, 2,875,057, 3,048,194, 3,265,506, 3,447,928, Farbkuppler eine Literaturversicht Agfa Mitteilung (Band II), pp. 112-126, 1961, etc. Among the compounds described in these references, acyl acetanilides such as benzoyl acetanilide and pivaloyl acetanilide are preferred.

Typical examples of the magenta coupler residue represented by Cp are described in U.S. Pat. Nos. 2,369,489, 2,343,703, 2,311,182, 2,600,788, 2,908,573, 3,062,653, 3,152,896, 3,519,429, 3,725,067, 4,540,654. Unexamined Published Japanese Patent Application No. 162548/1984, Agfa Mitteilung (Band II), ibid, pp. 112-126, 1961, etc. Among the compounds described in these references, pyrazolones and pyrazoloazoles (e.g. pyrazoloimidazole and pyrazolotriazole) are preperred.

Typical examples of the cyan coupler residue represented by Cp are described in U.S. Pat. Nos. 2,367,531, 2,423,730, 2,474,293, 2,772,162, 2,395,826, 3,002,836, 3,034,892, 3,041,236, 4,666,999, and Agfa Mitteilung (Band II), ibid, pp. 112-126, 1961, etc. Among the compounds described in these references, phenols and naphthols are preferred.

Typical examples of the coupler residue represented by Cp which forms a substantially colorless product are described in U.K. Patent No. 861,138, U.S. Pat. Nos. 3,632,345, 3,928,041, 3,958,993, 3,961,959, etc. Among the compounds described in these patents, cyclic carbonyl compounds are preferred.

The coupler residues described above may or may not be stabilized with non-diffusible groups. The coupler residues may be monomers or in a dimeric, oligomeric or polymeric form. The group $-(L)_n-A$ is bound to the coupler residue in either of the positions where the group released from the coupler upon reaction with the oxidized developing agent can be bound.

The linkage group represented by L may contain groups that are capable of controlling the rate of reaction between Cp and the oxidation product of a color developing agent, the rate of diffusion of $-(L)_n-A$ released from Cp and the rate of the release of A. Typical examples of such linkage group include those which release A by an intramolecular nucleophilic substitution reaction as described in U.S. Pat. No. 4,248,962 and Unexamined Published Japanese Patent Application No. 56837/1982 and those which release A along the conjugate chain by an electron transfer reaction as described in Unexamined Published Japanese Patent Applicatin Nos. 114946/1981 and 154234/1982. Other examples of the linkage group L are described in Unexamined Published Japanese Patent Application Nos. 188035/1982, 98728/1983, 206834/1984, 7429/1985, 214358/1985, 225844/1975, 229030/1985, 233649/1985, 237446/1985 and 237447/1985.

Examples of the linkage group represented by L and which are useful in the present invention include, but are not limited to, those which are represented by the following general formulas (II), (III) and (IV):

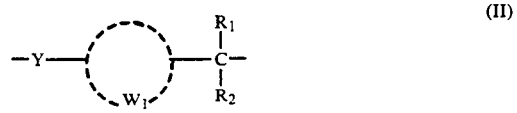

where $W_1$ is the atomic group necessary to form an optionally substituted benzene or naphthalene ring; Y is $-O-$, $-S-$ or $-N(R_3)$ and is bound at the coupling site to the coupler residue represented by Cp in the general formula (I); $R_1$, $R_2$ and $R_3$ are each a hydrogen atom, an alkyl group or an aryl group; and $-C(R_1)(R_2)-$ which is substituted in the position ortho or para to Y is bound to A;

where Y, $R_1$ and $R_2$ respectively have the same meanings as defined for Y, $R_1$ and $R_2$ in the general formula (II); $R_4$ is a hydrogen atom, an alkyl group, an aryl group, an acyl group, a sulfonyl group, an alkoxycarbonyl group or a heterocyclic residue; and $R_5$ is a hydrogen atom, an alkyl group, an aryl group, a heterocyclic residue, an alkoxy group, an amino group, an acid amido group, a sulfonamido group, a carboxyl group, an alkoxycarbonyl group, a carbamoyl group or a cyano group.

As in the general formula (II), the linkage group of the general formula (III) is bound via Y to the coupling site of the coupler residue represented by Cp in the general formula (I) and is bound to A via $-C(R_1)(R_2)-$.

An example of the linkage group that releases A by an intramolecular nucleophilic substitution reaction is represented by the following general formula (IV):

where Nu is a nucleophilic group having an electron-rich oxygen, sulfur or nitrogen atom and it is bound at the coupling site to the coupler residue represented by Cp in the general formula (I); E is an electrophilic group having an electron-lean carbonyl, thiocarbonyl, phosphinyl or thiophosphinyl group and it is bound to A; Z is a bonding group that sterically relates Nu and E and which, after Nu is released from the coupler residue represented by Cp in the general formula (I), undergoes an intramolecular nucleophilic reaction involving the formation of a 3- to 7-membered ring to thereby release A.

The organic group having a protected formyl group and which is represented by A in the general formula (I) may be exemplified by those which are represented by the following general formulas (V), (VI) and (VII):

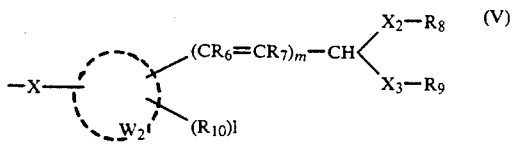

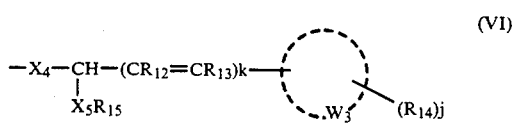

where m is an integer of 0-2; $R_6$ and $R_7$ each independently represents a hydrogen atom or a substituent, provided that when m is 2, $R_6$ and $R_7$ in ($CR_6=CR_7$) may be the same or different; the substituent represented by $R_6$ or $R_7$ may be exemplified by, but not limited to, an alkyl group (e.g. methyl or ethyl), an alkoxy group (e.g. methoxy or ethoxy), an amino group, an alkylamino group (e.g. dimethylamino, di(hydroxyethyl)-amino, acetoxyethylamino or cyanoethylamino), an alkylcarbamoyl group, an arylcarbamoyl group, an acylamino group, aroylamino group, a ureido group, a sulfonylamino group (e.g. methylsulfonylamino or phenylsulfonylamino), a nitro group, a cyano group, an alkylsulfonyl group (e.g. methylsulfonyl), an alkoxycarbonyl group (e.g. methoxycarbonyl or ethoxycarbonyl), a phenoxycarbonyl group (e.g. phenoxycarbonyl or p-chlorophenoxycarbonyl), an alkoxysulfonyl group (e.g. butoxysulfonyl), and an aryloxysulfonyl group (e.g. phenoxysulfonyl).

In the general formula (V), $R_8$ and $R_9$ each represents an alkyl group, an aryl group, an alkylsulfonyl group, an arylsulfonyl group, an acyl group, etc., provided that $R_8$ and $R_9$ may combine together to form a cyclic structure.

In the general formula (V), $R_{10}$ typically represents a straight or branched alkyl group having 1-30 carbon atoms, a halogen atom, an aryl group, an alkoxy group, an aryloxy group, an alkylthio group, an arylthio group, a carbamoyl group, a sulfamoyl group, an acylamino group, a sulfonylamino group, an alkyloxycarbamoyl group, a nitro group, a cyano group, a hydroxyl group, an amino group, an alkylamino group or an arylamino group but these are by no means the sole examples of the referent of $R_{10}$; l is an integer of 1-4 and $R_{10}$ may be the same or different when l is 2 or more; at least one of $R_6$, $R_7$ and $R_{10}$ has a group with 10-40 carbon atoms.

In the general formula (V), X, $X_2$ and $X_3$ each represents an oxygen atom, a sulfur atom or a divalent bonding group such as $NR_{11}$, where $R_{11}$ is an alkyl group, an aryl group, an alkylsulfonyl group, an arylsulfonyl group, an acyl group, an acylamino group, etc. Preferred combinations of $X_2$ and $X_3$ include the combination of two oxygen atoms, the combination of an oxygen atom and a sulfur atom, and the combination of two sulfur atoms. The group $X_2$-$R_8$ or $X_3$-$R_9$ is preferably such that they will not cause adverse effects on photographic performance when they are released into the emulsion layer.

In the general formula (V), $W_2$ represents a group capable of forming a 5- or 6-membered aromatic or heteroaromatic ring. The aromatic ring or heteroaromatic ring may have a condensed ring attached thereto. Preferred but non-limiting examples of such rings include benzene, naphthalene, pyridine, pyrimidine, pyrazole, imidazole, oxazole, thiazole, isoxazole, isothiazole, furan, thiophene, indole, benzofuran and benzothiophene. Among these, benzene and pyrazole are particularly preferred aromatic or heteroaromatic rings.

where k is an integer of 0-2; $R_{12}$ and $R_{13}$ each independently represents a hydrogen atom or a substituent, provided that when k is 2, $R_{12}$ and $R_{13}$ in ($CR_{12}=CR_{13}$) may be the same or different; the substituent represented by $R_{12}$ or $R_{13}$ may be exemplified by, but not limited to, an alkyl group (e.g. methyl or ethyl), an alkoxy group (e.g. methoxy or ethoxy), an amino group, an alkylamino group (e.g. dimethylamino, di(hydroxyethyl)amino, acetoxyethylamino or cyanoethylamino), an alkylcarbamoyl group, an arylcarbamoyl group, an acylamino group, an aroylamino group, a ureido group, a sulfonylamino group (e.g. methylsulfonylamino or phenylsulfonylamino), a nitro group, a cyano group, an alkylsulfonyl group (e.g. methylsulfonyl), an alkoxycarbonyl group (e.g. methoxycarbonyl or ethoxycarbonyl), a substituted or unsubstituted phenoxycarbonyl group (e.g. phenoxycarbonyl or p-chlorophenoxycarbonyl), an alkoxysulfonyl group (e.g. butoxysulfonyl), and an aryloxysulfonyl group (e.g. phenoxysulfonyl).

In the general formula (VI), $R_{14}$ has the same meaning as defined for $R_{10}$ in the general formula (V); j is an integer of 1-5, provided that when j is 2 or more, $R_{14}$ may be the same or different; at least one of $R_{12}$, $R_{13}$ and $R_{14}$ has a group with 10-40 carbon atoms; $R_{15}$ is an alkyl group, an aryl group, an alkylsulfonyl group, an arylsulfonyl group, etc.; $X_4$ and $X_5$ each represents an oxygen atom, a sulfur atom or a divalent bonding group such as $NR_{16}$, where $R_{16}$ is preferably an alkyl group, an aryl group, an alkylsulfonyl group, an arylsulfonyl group, an acyl group, an acylamino group, etc; and $W_3$ has the same meaning as defined for $W_2$ in the general formula (V).

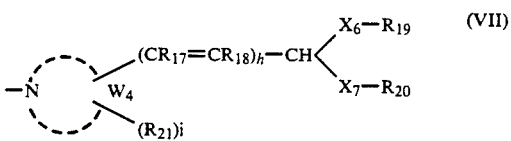

where $R_{17}$ and $R_{18}$ respectively have the same meanings as defined for $R_6$ and $R_7$ in the general formula (V); $R_{19}$ and $R_{20}$ respectively have the same meanings as defined for $R_8$ and $R_9$ in the general formula (V); $R_{21}$ has the same meaning as defined of $R_{10}$ in the general formula (V); h is an integer of 0-2; and i is an integer of 0-4.

In the general formula (VII),

represents a nitrogenous 5- or 6-membered hetero ring and is bound via the nitrogen atom to Cp or L in the general formula (I). Examples of the 5- or 6-membered hetero ring represented by

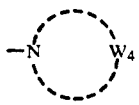

include pyrazole, imidazole, 1,2,3-triazole, 1,2,4'-triazole, tetrazole, pyridinone, pyrimidinone, uracil, pyrazinone and pyridazinone. These hetero rings may be condensed to any other aromatic rings in a position where they can be condensed.

In the general formula (VII), $X_6$ and $X_7$ each represents an oxygen atom, a sulfur atom or a divalent bonding group such as $NR_{22}$, where $R_{22}$ is an alkyl group, an aryl group, an alkylsulfonyl group, an arylsulfonyl group, an acyl group, an acylamino group, etc.

The novel couplers used in the present invention would generate dyes by the following mechanism:

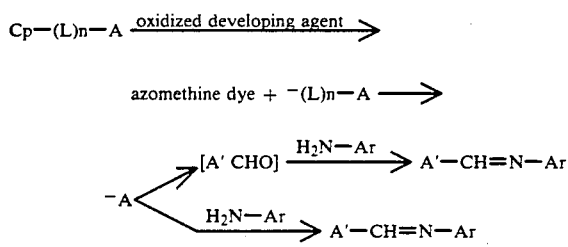

In this scheme, Cp, L, A and n have the same meanings as already defined above; A'CHO represents the aldehyde that can be generated by A as it leaves the coupler, provided that A'CHO need not necessarily be generated in the process of dye formation in a processing solution. Consider, for example, the case where the group represented by the general formula (V) is released as A; the formyl protecting group would undergo cleavage by electron transfer according to the following scheme:

where Nu represents a nucleophilic agent present in a processing solution. When Nu is a hydroxide ion, it forms aldehyde and reacts with a developing agent to form a dye. When Nu represents a developing agent, the desired dye would be obtained without forming aldehyde.

Unexamined Published Japanese Patent Application No. 52148/1989 describes a coupler that forms a masking dye and that has a leaving group with a formyl group incorporated thereinto. However, the formyl group in the leaving group in this coupler is not protected. The coupler reacts directly with a color developing agent in unexposed areas to form an insoluble masking dye. In exposed areas, the coupler enters into a coupling reaction with the oxidized color developing agent to form not only an image forming dye but also a water-soluble dye that is washed away from the image area. Hence, this coupler is entirely different from the novel couplers to be used in the present invention which do not form a dye in unexposed areas but which form, in exposed areas, a dye that is to remain in the light-sensitive material.

Unexamined Published Japanese Patent Application No. 154057/1989 teaches the release of two molecules of a photographically useful group using a coupler that releases two molecules of such photographically useful group from a leaving group that is eliminated upon reaction with the oxidation product of a developing agent. According to the patent, supra, a color photographic material of high sensitivity can be obtained that is improved in sharpness, granularity, color reproduction and desilvering quality. However, no recognition is suggested that concerns the formation of a parsistent dye in the photographic material from the leaving group that has released the photographically useful group. Hence, the coupler taught by this patent is also entirely different from the novel couplers to be used in the present invention which form a dye that is to remain in the photographic material.

Specific but non-limiting examples of the coupler that can be used in the present invention are listed below.

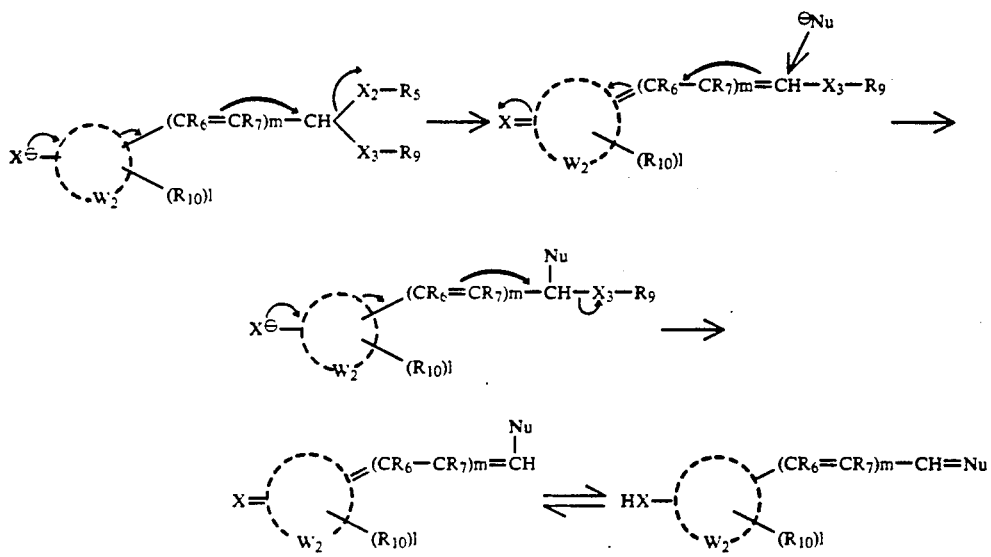

Exemplary compound
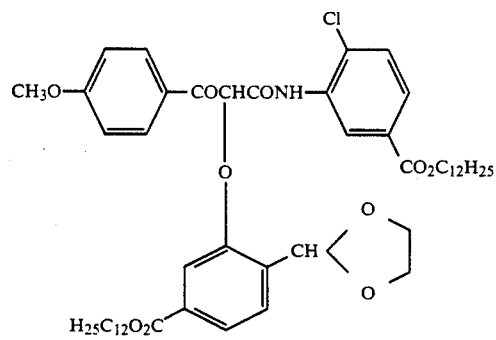
(1)
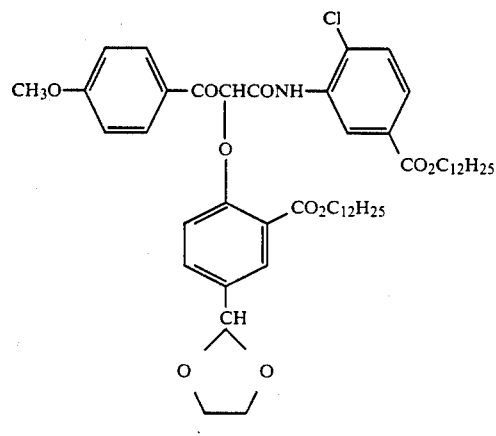
(2)
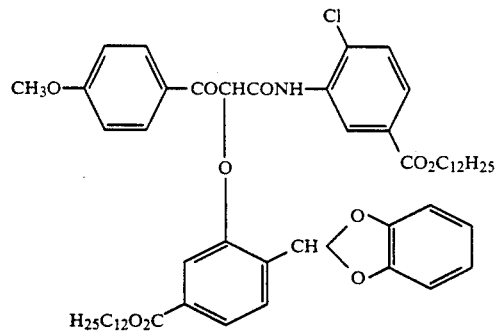
(3)
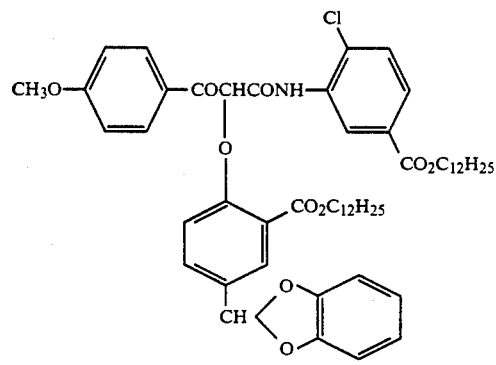
(4)

-continued
Exemplary compound
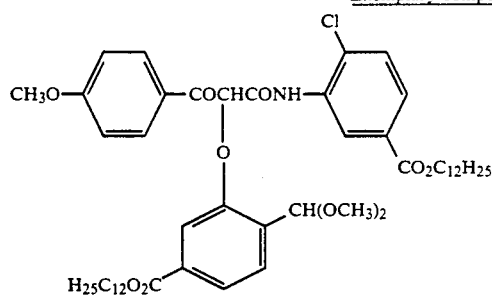
(5)
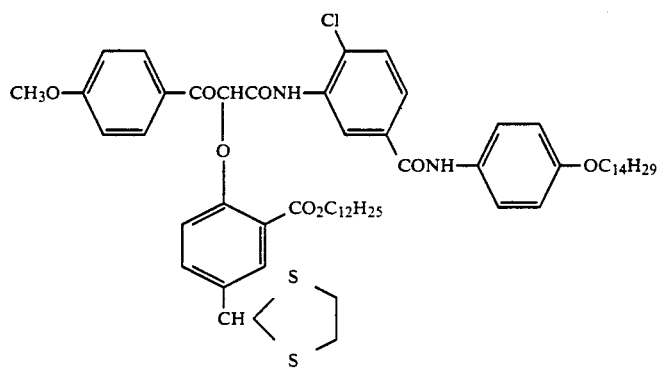
(6)
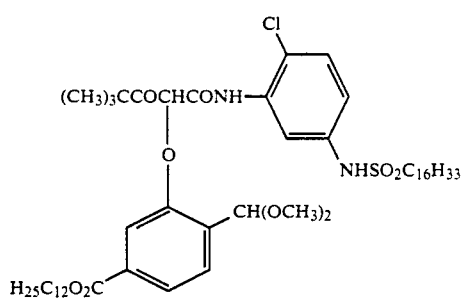
(7)
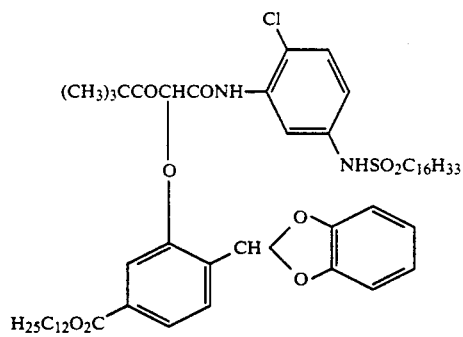
(8)
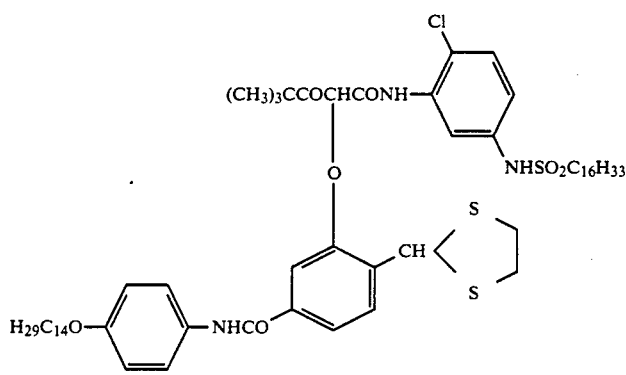
(9)

-continued
Exemplary compound
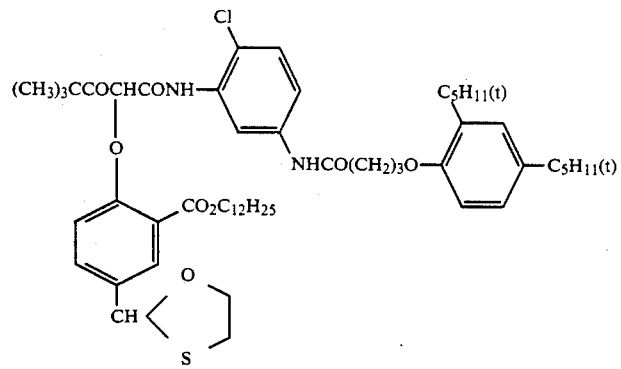
(10)
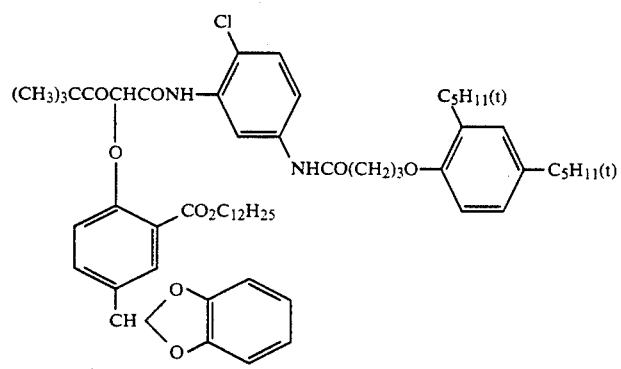
(11)
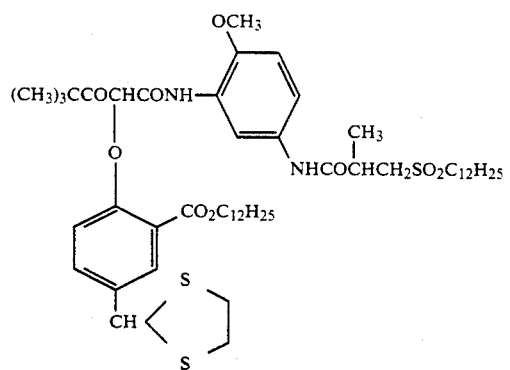
(12)
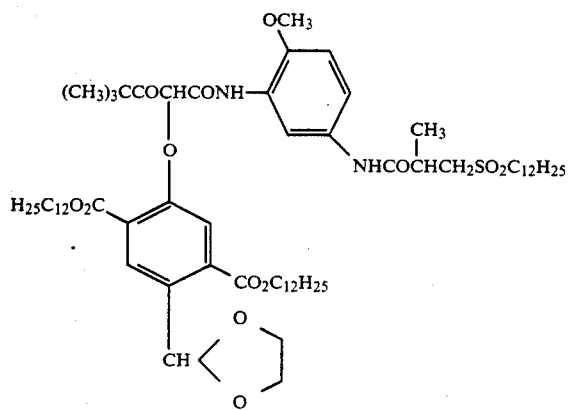
(13)

-continued
Exemplary compound
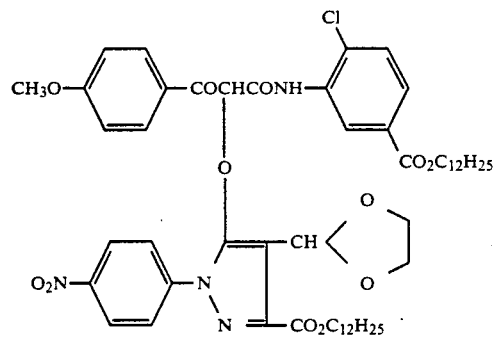
(14)
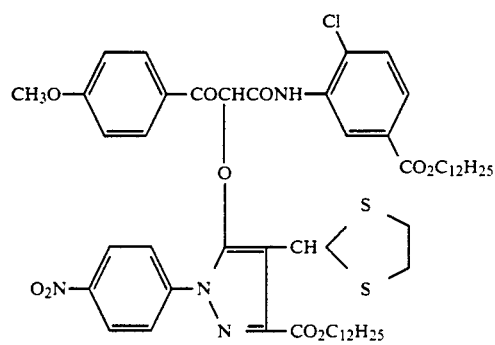
(15)
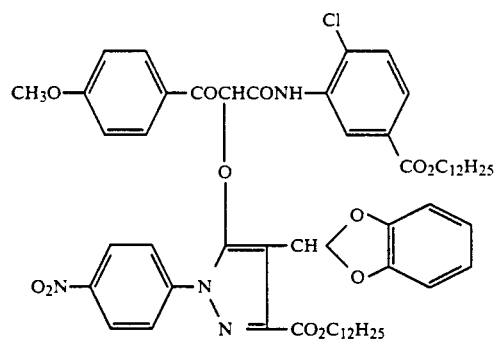
(16)
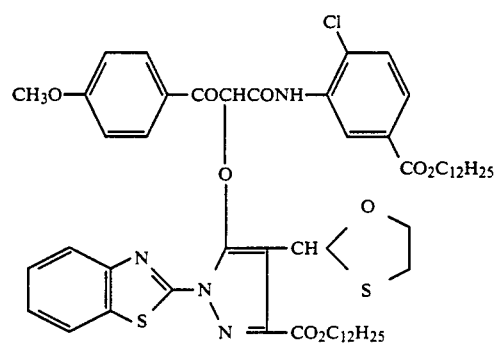
(17)

-continued
Exemplary compound
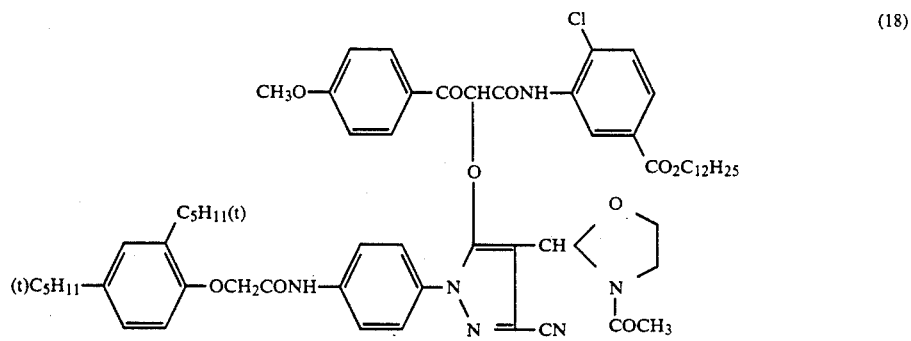
(18)
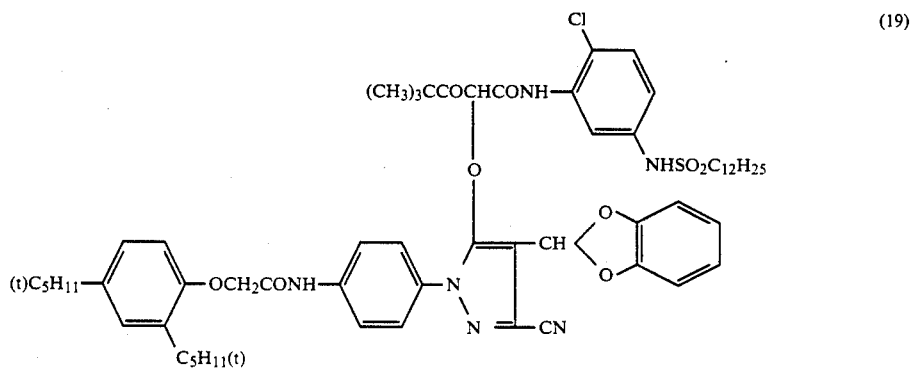
(19)
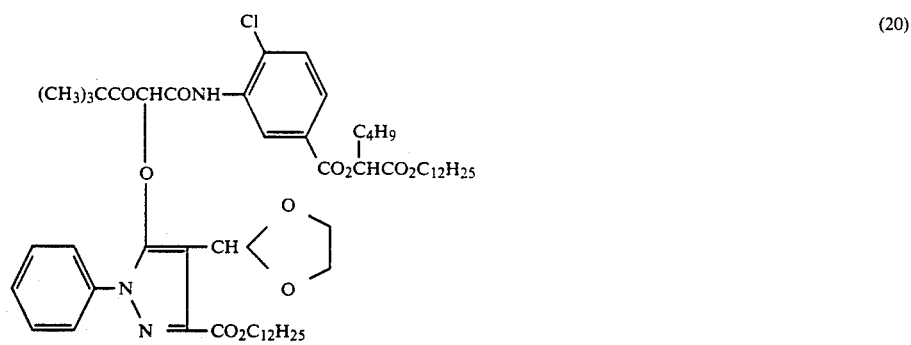
(20)
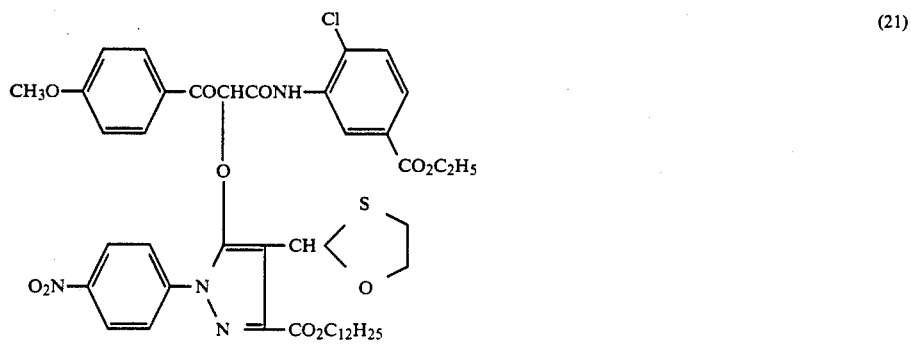
(21)

-continued
Exemplary compound
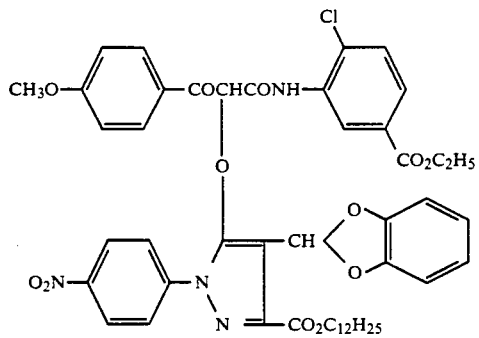
(22)
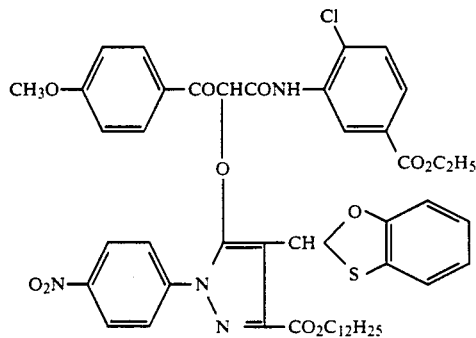
(23)
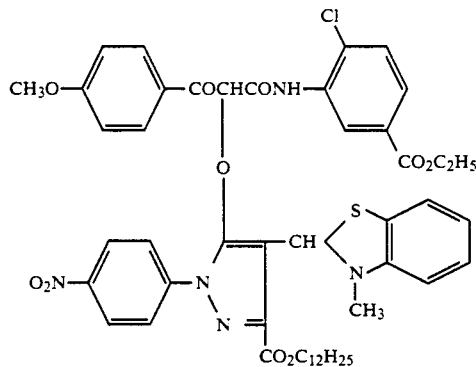
(24)
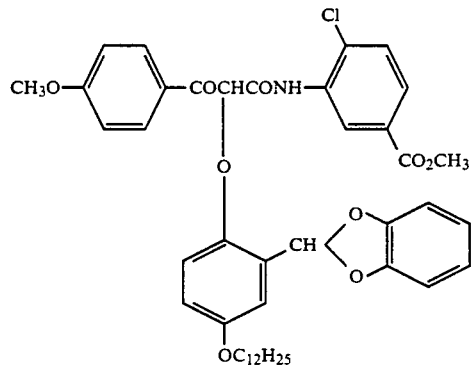
(25)

-continued
Exemplary compound
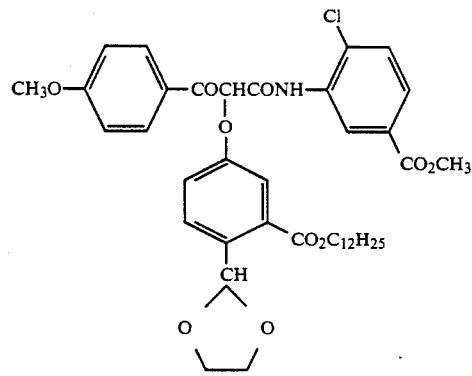
(26)
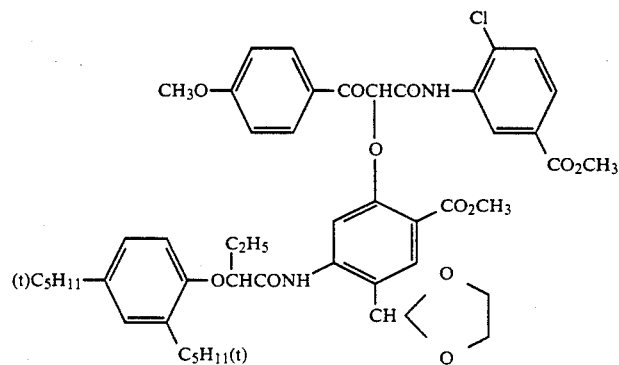
(27)
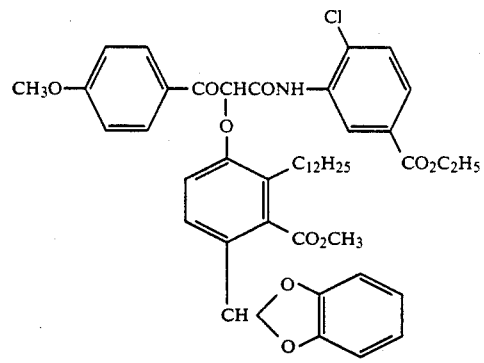
(28)
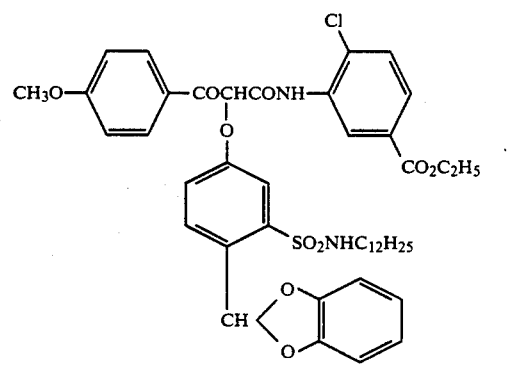
(29)

-continued
Exemplary compound
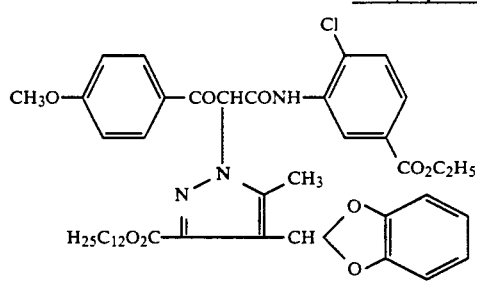 (30)
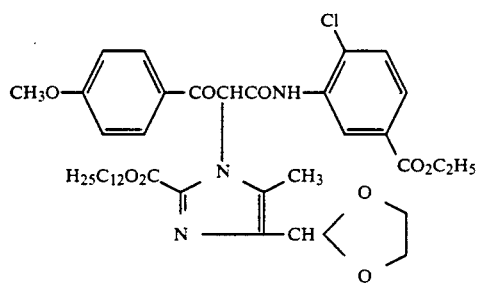 (31)
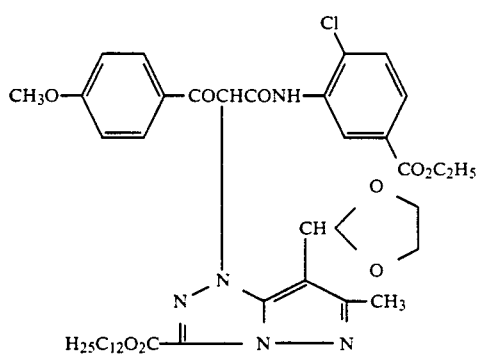 (32)
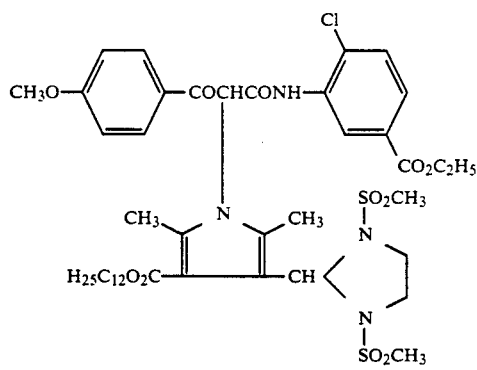 (33)
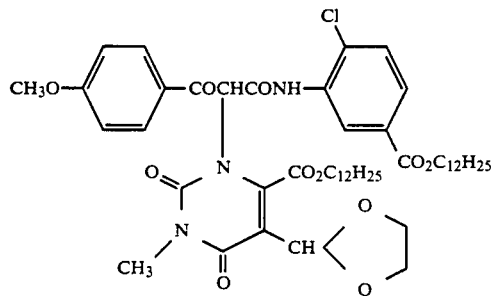 (34)

-continued
Exemplary compound
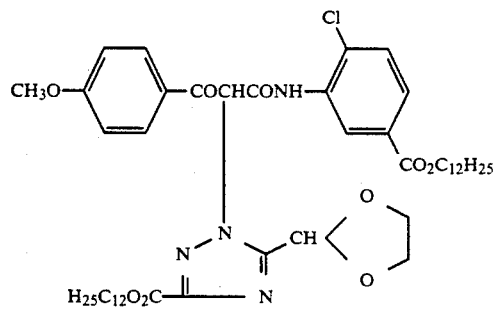
(35)
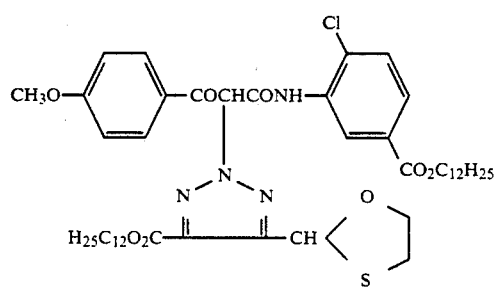
(36)
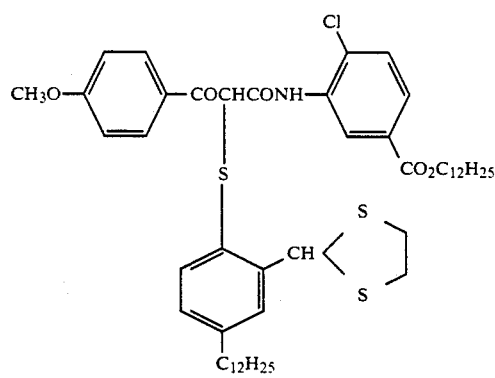
(37)
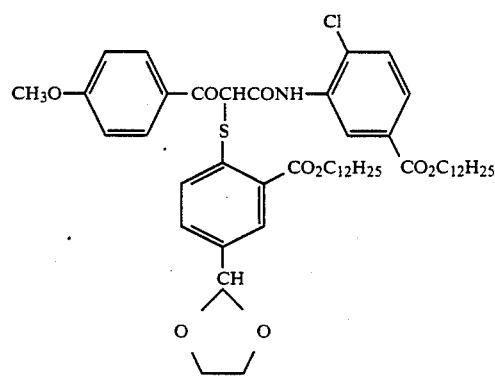
(38)

-continued
Exemplary compound
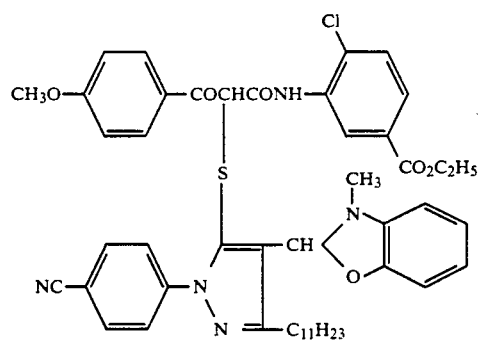
(39)
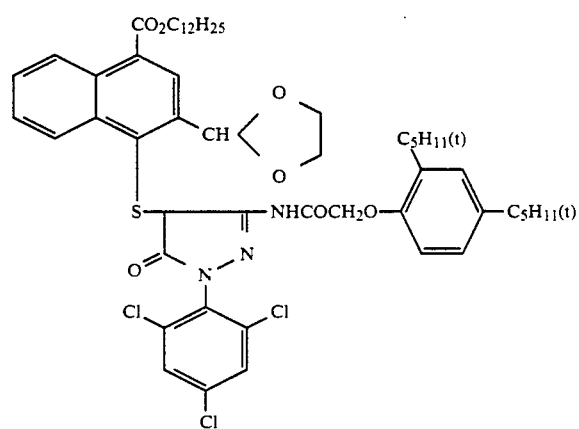
(40)
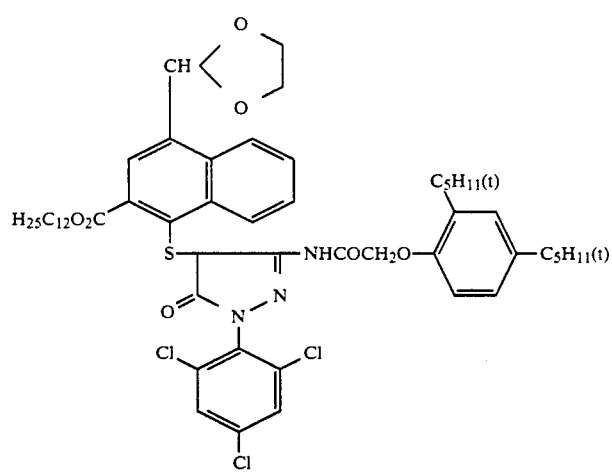
(41)
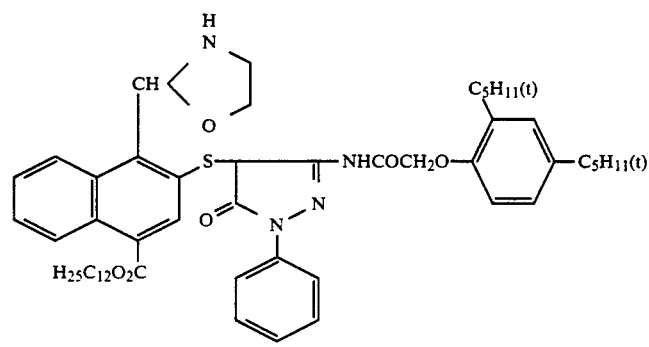
(42)

-continued
Exemplary compound
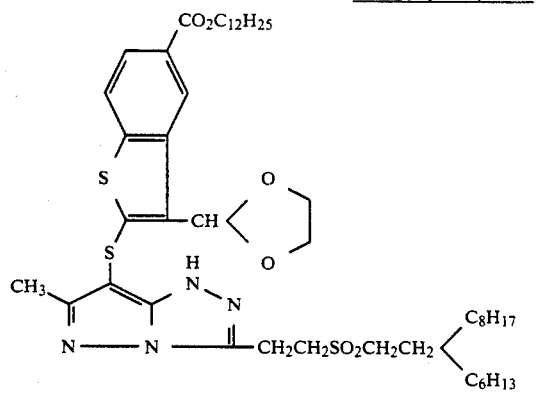 (43)
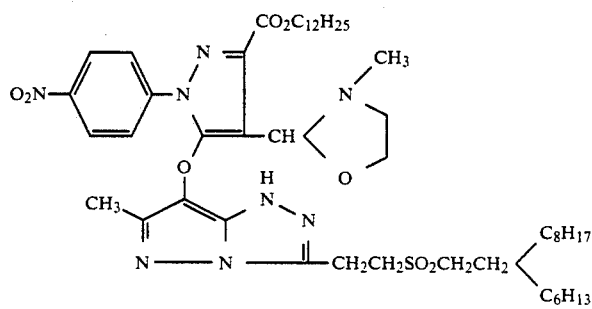 (44)
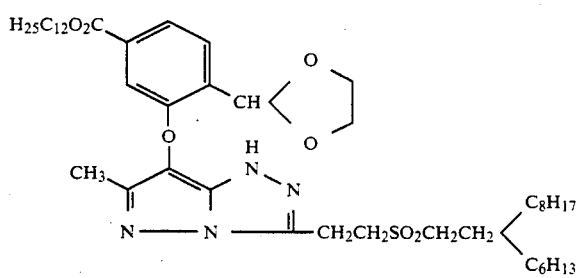 (45)
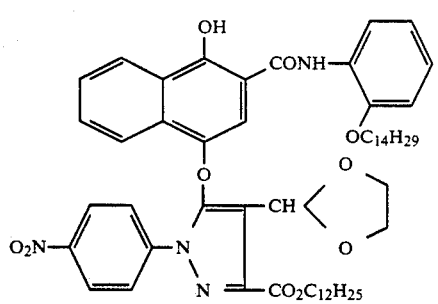 (46)
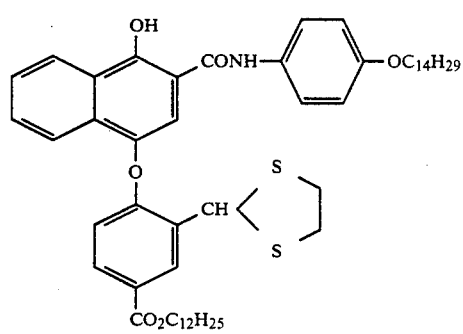 (47)

Exemplary compound
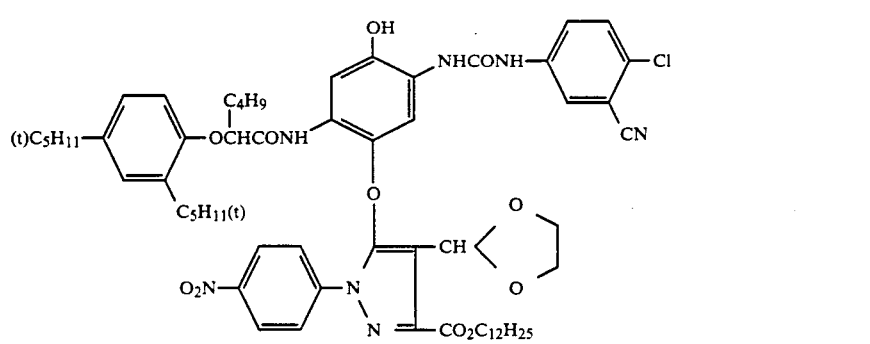 (48)
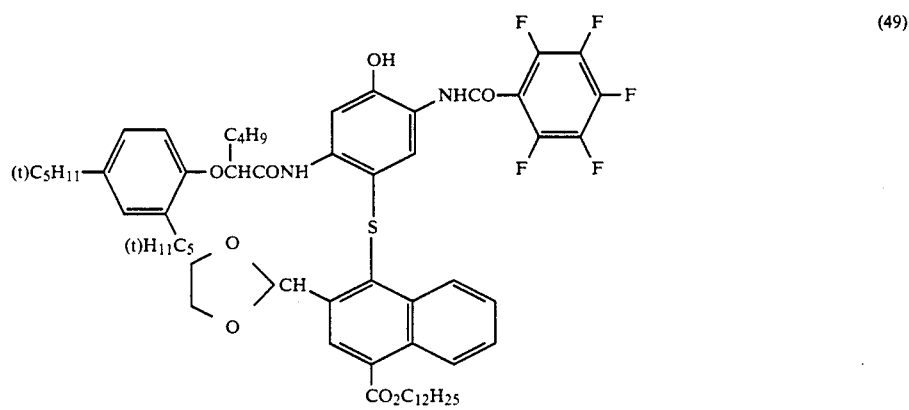 (49)
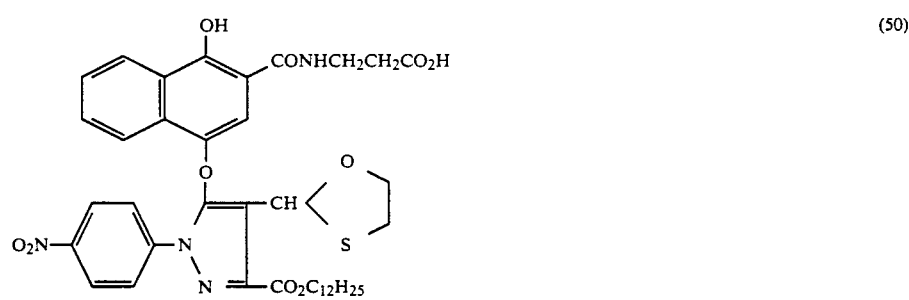 (50)
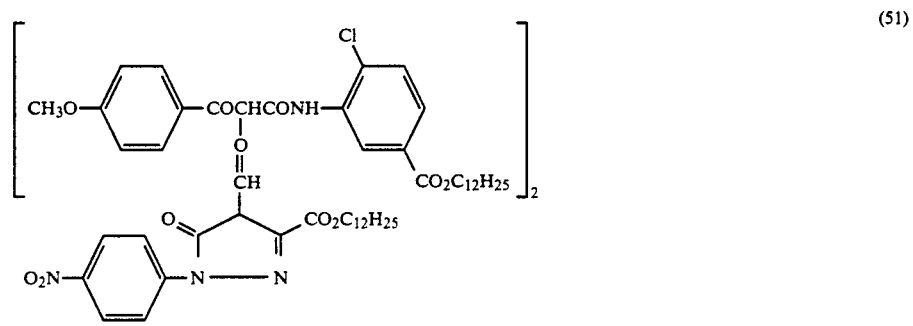 (51)

-continued
Exemplary compound
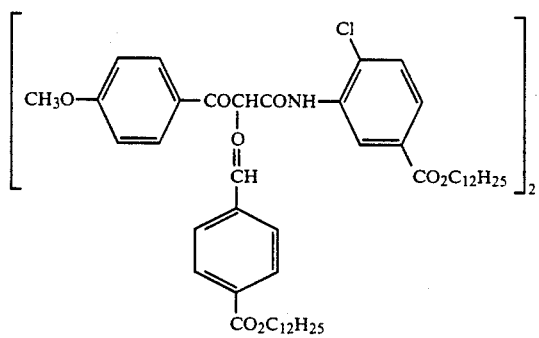 (52)
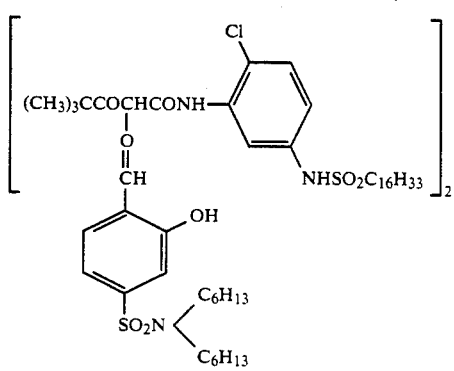 (53)
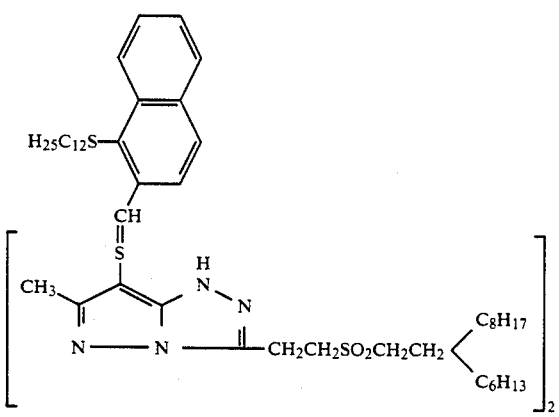 (54)
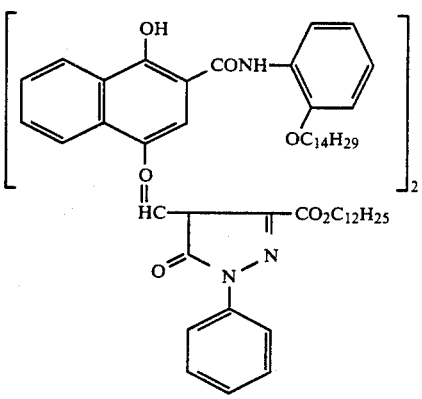 (55)

-continued
Exemplary compound
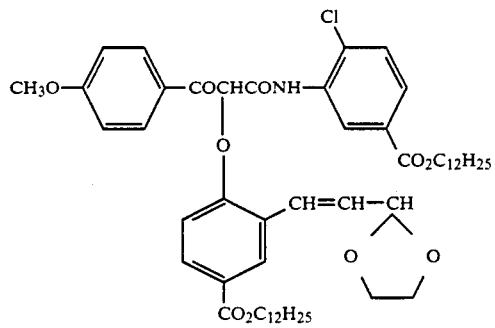
(56)
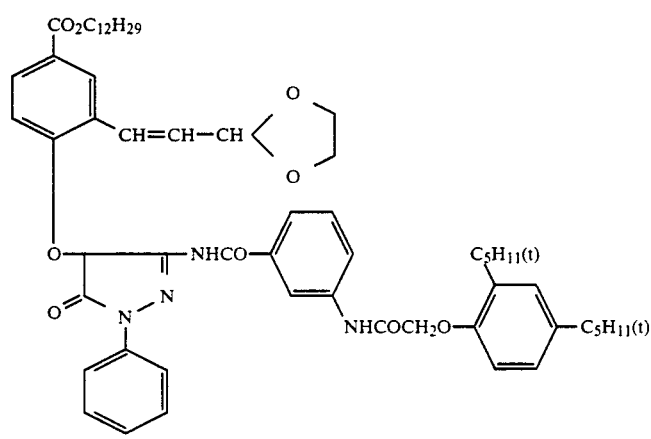
(57)
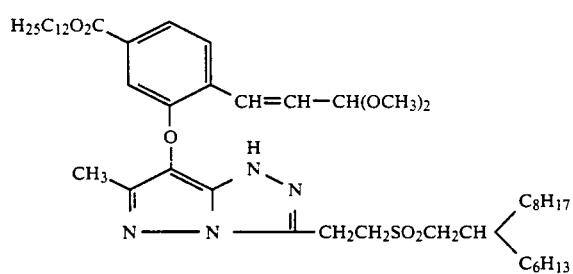
(58)
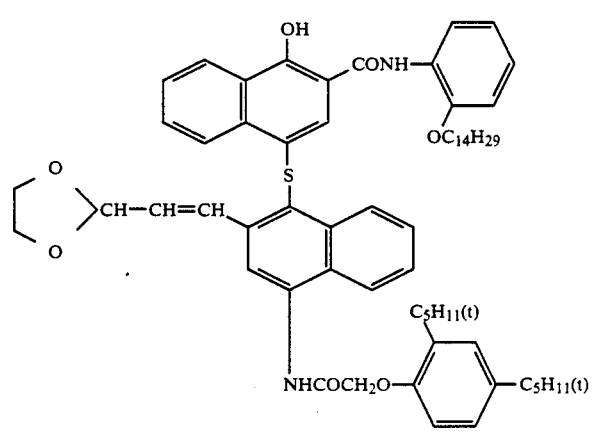
(59)

-continued
Exemplary compound
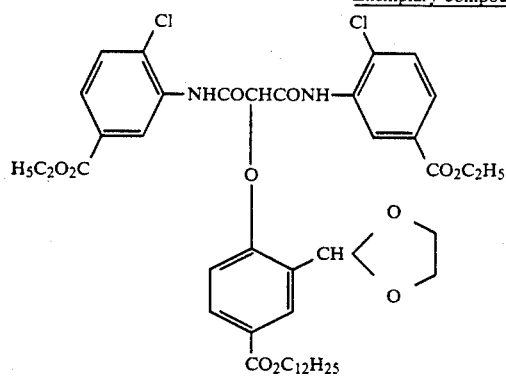
(60)
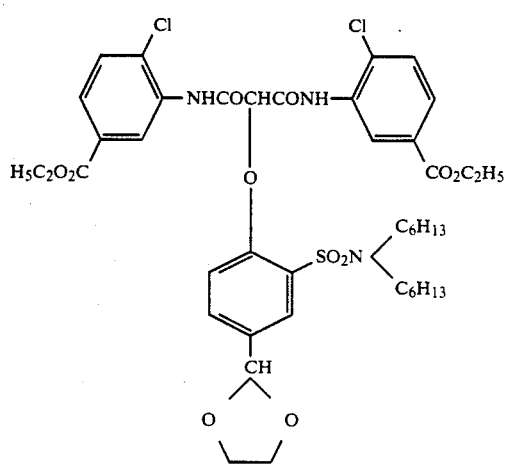
(61)
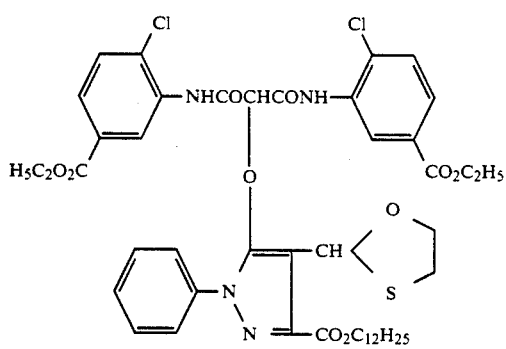
(62)
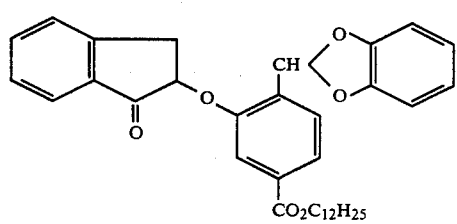
(63)
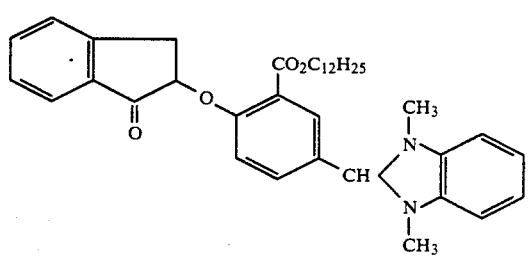
(64)

-continued
Exemplary compound
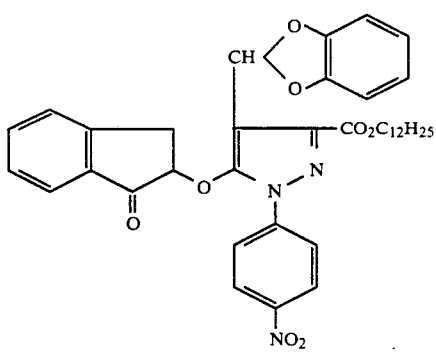
(65)
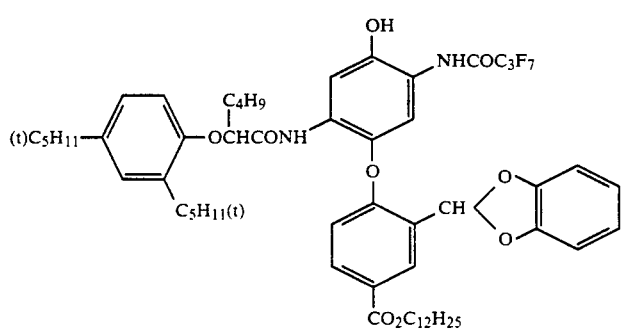
(66)
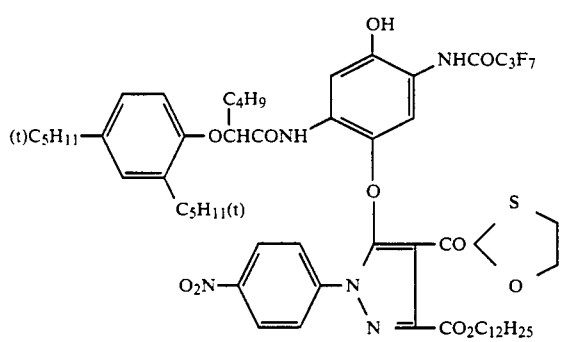
(67)
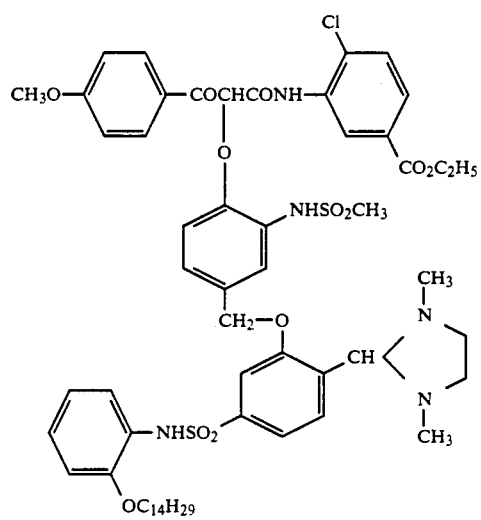
(68)

-continued
Exemplary compound
(69)
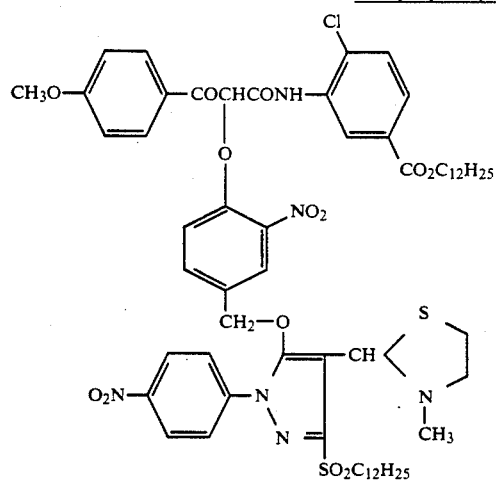
(70)
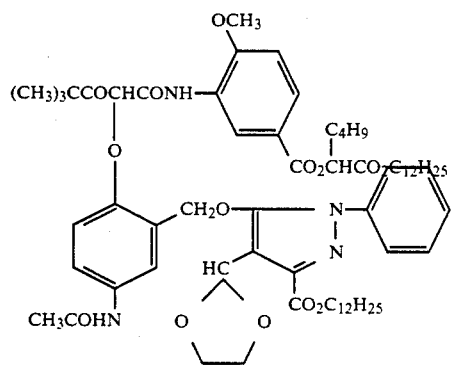
(71)
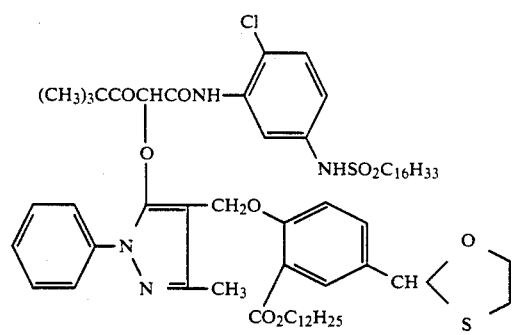
(72)
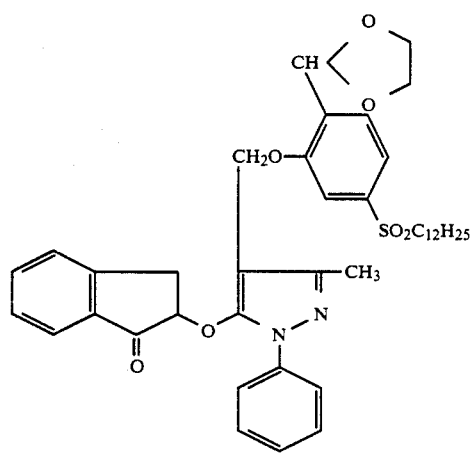

-continued
Exemplary compound
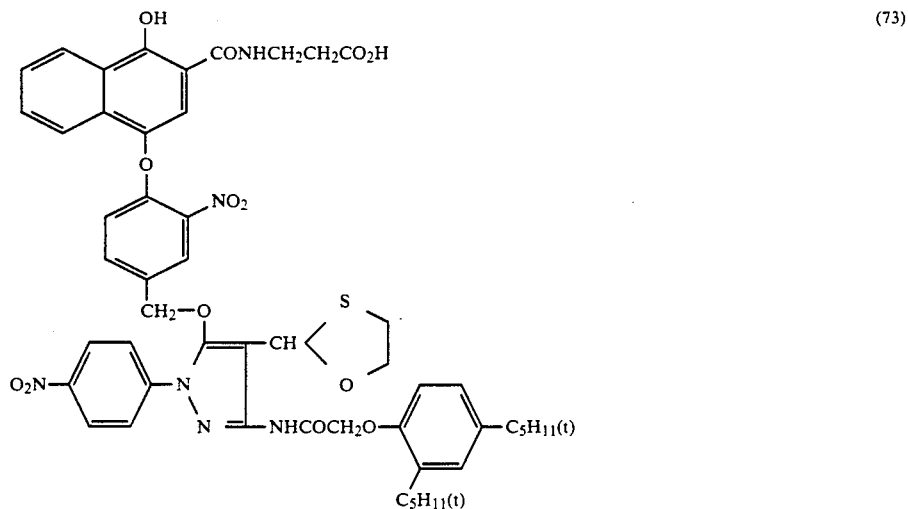
(73)
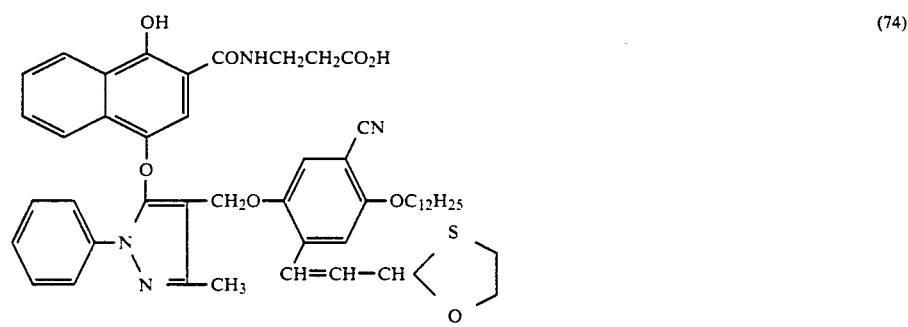
(74)
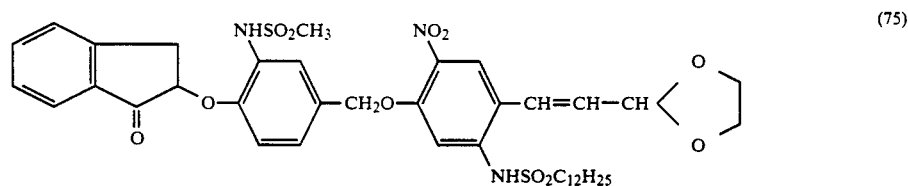
(75)
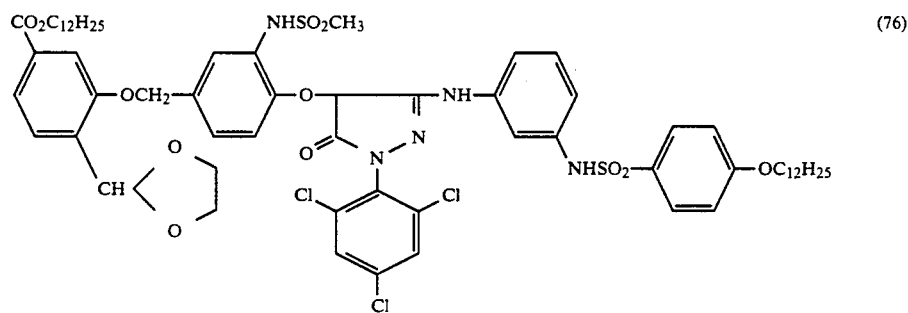
(76)

-continued
Exemplary compound
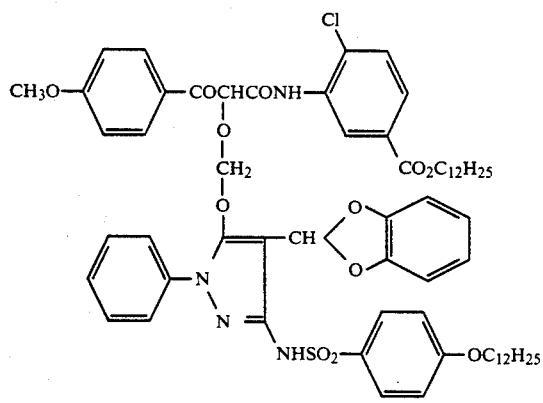 (77)
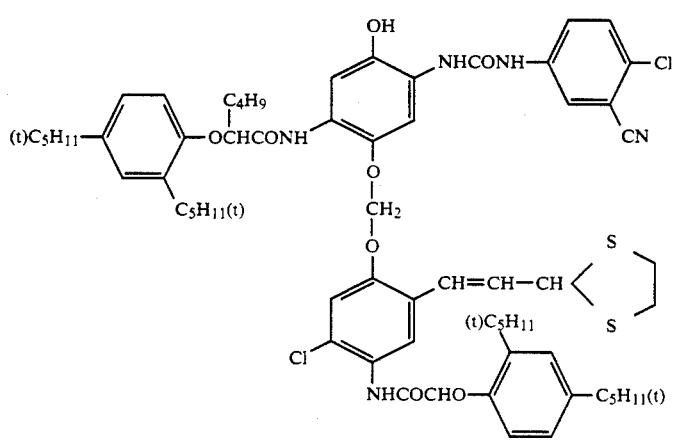 (78)
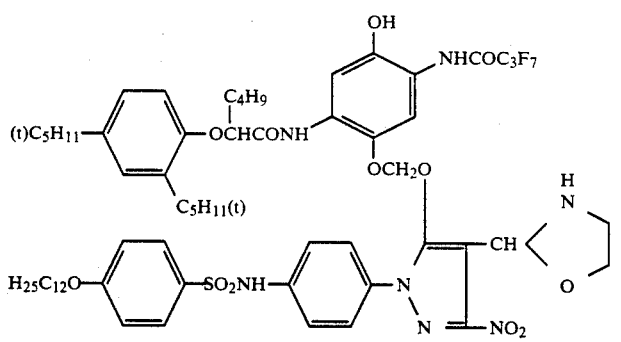 (79)
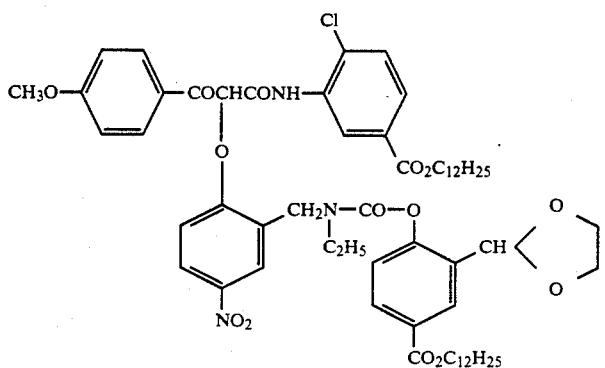 (80)

-continued

Exemplary compound (81)

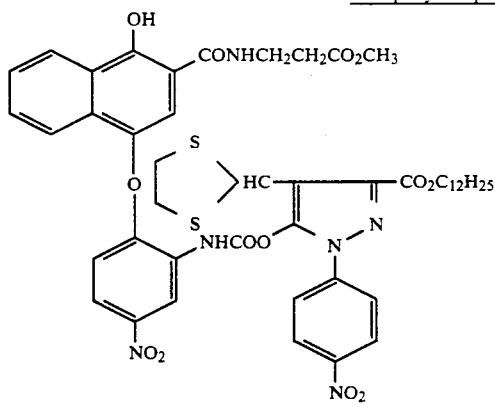

Couplers represented by the general formula (I) for use in the present invention can be prepared by methods known in the industry of organic synthesis. A specific example of synthesis is described below.

Synthesis Example (1)
Synthesis of exemplary compound (16):

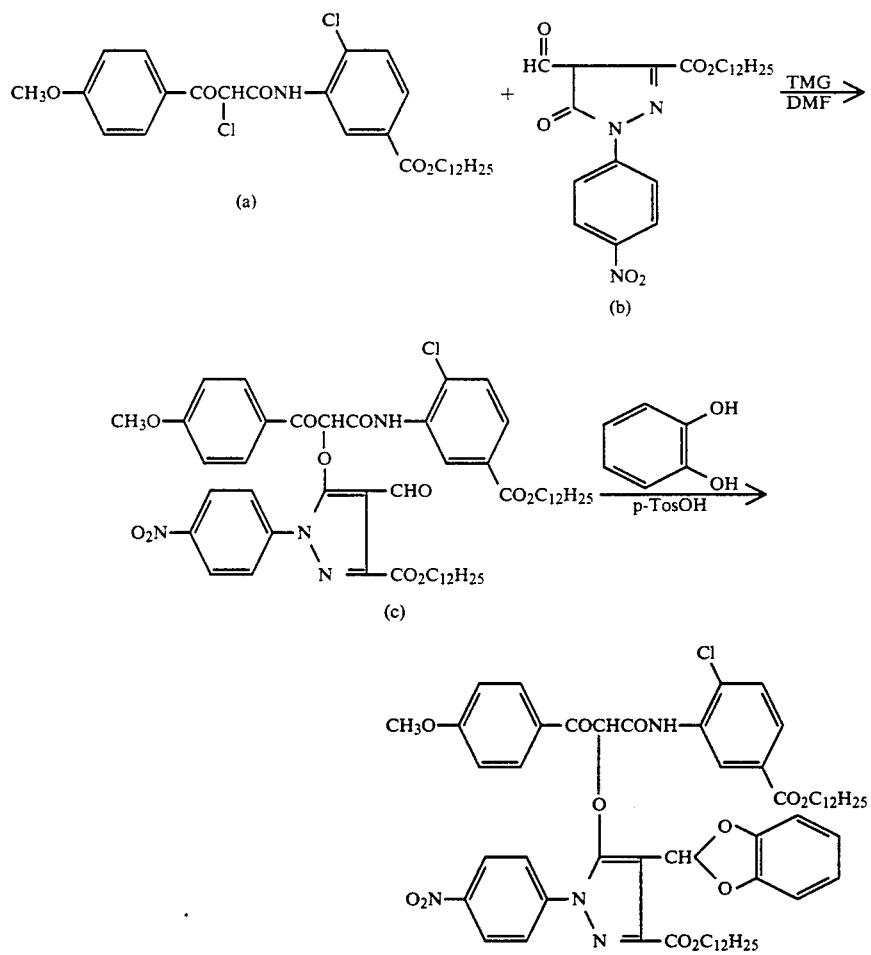

Exemplary compound (16)

α-(4-Methoxybenzoyl)-α-chloro-2-chloro-5-dodecyloxycarbonyl acetanilide (a) (3.29 g, 6 mmol) and dodecyl 4-formyl-5-hydroxy-1-(4-nitrophenyl)-pyrazole-3-carboxylate (b) (2.67 g, 6 mmol) are dissolved in 20 ml of dimethylformamide (DMF) and the solution is maintained at 50°-55° C. in a nitrogen atmosphere. A solution of 1,1,3,3-tetramethylguanidine (TMG) (1.38 g, 12 mmol) dissolved in DMF (6 ml) is added dropwise. After standing at 50°-60° C. for 3 h, the mixture is cooled, diluted with ethyl acetate, washed with water, dried with $MgSO_4$ and concentrated to an oil. The oil is subjected to chromatography on a silica gel column and eluted with ethyl acetate/- hexane. The resulting fraction is purified to obtain 1.53 g (49%) of a colorless crystal (c).

A portion (2.87 g, 3 mmol) of (c) and pyrocatechol (0.55 g, 5 mmol) are dissolved in toluene (50 ml). After adding 10 mg of p-toluenesulfonic acid, the mixture is heated under reflux for 10 h using a Dean-Stark tube. The reaction solution is washed first with 1N NaHCO$_3$, then with water, and dried with MgSO$_4$ to obtain an oil. The oil is subjected to chromatography on a silica gel column and eluted with ethyl acetate/hexane. The resulting fraction is purified to obtain a colorless crystal of the end compound (16). By NMR and mass spectra, the compound is identified as the desired exemplary compound (16).

The photographic material in which the couplers for use in the present invention are to be incorporated may have a single photographic constituent layer unit (containing only one silver halide emulsion layer on a support) or a multi-layered and multi-color photographic constituent layer unit.

The silver halide emulsion layer may contain not only the couplers but also other photographic couplers such as ordinary dye forming couplers that form dyes of the same color shades, restrainer releasing couplers, and masking couplers. A typical example of the preferred photographic material is such that a support is overlaid with a red-sensitive silver halide emulsion layer containing one or more cyan dye forming couplers, a green-sensitive silver halide emulsion layer containing one or more magenta dye forming couplers, and a blue-sensitive silver halide emulsion layer containing one or more yellow dye forming couplers.

Each of these silver halide emulsion layers may be composed of two or more sub-layers which may contain the photographic couplers described above.

The couplers represented by the general formula (I) for specific use in the present invention and the other photographic couplers described above may be used as admixtures in one light-sensitive layer. Alternatively, the same compound may be added in two or more layers.

The couplers (I) are preferably added in amounts that range from $2 \times 10^{-5}$ to $1 \times 10^{-3}$ mole per square meter of the layer in which they are incorporated. If they are to be used together with couplers that form dyes of the same color shades, the latter is preferably added in amounts ranging from 0.001 to 20 moles per mole of the coupler (I).

Couplers can be incorporated into the photographic material by various known methods of dispersion such as a solid dispersion method or an alkali dispersion method, preferably by a latex dispersion method, more preferably by an oil-in-water dispersion method. According to the oil-in water dispersion method, a coupler of interest is dissolved in either a high-boiling ($\geq 175°$ C.) organic solvent or a low-boiling organic solvent or both; thereafter, the dispersion is dispersed finely in an aqueous medium such as water or an aqueous gelatin solution in the presence of a surfactant. Examples of the high-boiling organic solvent are described in U.S. Pat. No. 2,322,027 and other prior patents. The dispersing operation may involve phase inversion. The dispersion may be used as a coating solution after the auxiliary solvent is removed or reduced in amount by a suitable technique such as distillation, noodle washing or ultrafiltration.

Gelatin is advantageously used as a binder or protective colloid in emulsion layers or intermediate layers that constitute the photographic material of the present invention. Other hydrophilic colloids may be used either independently or in combination with gelatin.

Silver halide emulsion layers in the photographic material of the present invention may use any silver halide composition such as silver bromide, silver iodobromide, silver iodochlorobromide, silver chlorobromide or silver chloride. The silver halide to be preferably used in picture-taking color photographic materials is silver iodobromide or silver iodochlorobromide that contain no more than about 15 mol % of silver iodide. Silver iodobromide containing ca. 2–12 mol % of silver iodide is used with particular preference. Silver bromide, silver chlorobromide and silver iodochlorobromide are preferably used with photographic materials for making color prints.

The silver halide grains in photographic emulsions may be "regular" grains having regular crystallographic forms such as cubes, octahedra and tetradecahedra. Also usable are grains having anomalous shapes such as spheres or crystal defects such as twinned faces, or combinations of these shapes.

The silver halide grains to be used in the present invention may be fine grains not larger than ca. 0.1 microns or they may be large-sized grains with a projected area having a diameter of up to ca. 10 microns. The silver halide grains may comprise a monodispersed emulsion having a narrow size distribution or a polydispersed emulsion having a broad distribution.

A typical monodispersed emulsion is such that it comprises silver halide grains having an average grain size greater than ca. 0.1 micron, with at least ca. 95 wt % of said grains falling within ±40% of the average grain size. The emulsion that is preferably used in the present invention is such that it comprises silver halide grains having an average grain size of ca. 0.25–2 microns, with at least ca. 95% in weight or number of the grains falling within the range of ±20% of the average grain size.

Tabular grains having an aspect ratio of at least ca. 5 can also be used. Desired tabular grains can be easily prepared by known methods such as those described in E. Gutoff, Photogr. Sci. Eng., 14, 248–257 (1970), U.S. Pat. Nos. 4,434,226, 4,414,310, 4,433,048, 4,439,520, and U.K. Patent No. 2,112,157.

The emulsion to be used in the present invention is usually subjected to preliminary physical ripening, chemical ripening and spectral sensitization.

Additives that are described in Research Disclosure Nos. 17643 and 18716 may be used in the present invention.

Any of the supports that are customarily used with photographic materials may be employed in the present invention and they include films of cellulose acetate, polyvinyl acetal, polyethylene terephthalate and other high-molecular weight polymers, as well as flexible supports such as paper base.

For color development of the photographic material of the present invention, color developing solutions of a customary composition that contain aromatic primary amino developing agents may be used. Other known compounds for use in developing solutions may be incorporated in the color developing solution and examples of such auxiliary additives include alkali agents and buffers. Exemplary alkali agents and buffers include sodium hydroxide, potassium hydroxide, sodium carbonate, potassium carbonate, sodium tertiary phosphate, potassium tertiary phosphate, potassium metaborate and borax, which may be used either on their own or as admixtures. Sulfites (e.g. sodium sulfite, potassium sulfite, potassium bisulfite and sodium bisulfite) and hydroxylamine which are conventionally used as preservatives may also be incorporated in the color developing solutions. Any development accelerators may be added, as required, to the color developing solutions.

After color development, the photographic emulsion layers are usually bleached and fixed. Bleaching may be performed simultaneously with fixing or the two steps may be conducted separately. Particularly useful bleaching agents are potassium ferricyanide, ethylenediaminetetraacetic acid iron (III) sodium, ethylenediaminetetraacetic acid iron (III) ammonium and diethylenetriaminepentaacetic acid iron (III) ammonium. Aminopolycarboxylic acid iron (III) complex salts are useful not only in independent bleaching solutions but also in mono-bath bleach-fixing solutions. Various additives including the bleaching accelerators described in U.S. Pat. Nos. 3,042,520, 3,241,966, Examined Japanese Patent Publication Nos. 8506/1970 and 8836/1970 may be added to the bleaching or bleach-fixing solutions. The fixing bath contains an ammonium, sodium or potassium salt of thiosulfuric acid as a fixing agent in an amount of ca. 30–200 g/L. Other additives that may be incorporated in the fixing bath include stabilizers such as sulfites and isomeric bisulfites, hardeners such potassium alumn, and pH buffers such as acetates, borates, phosphates and carbonates. The fixing solution preferably has a pH of 3–10, more preferably 5–9.

The following examples are provided for the purpose of further illustrating the present invention but are in no way to be taken as limiting.

The compounds used in the examples are first listed below.

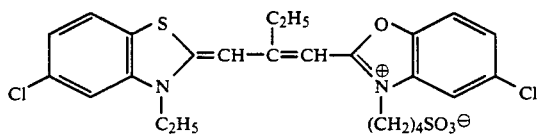

S-1

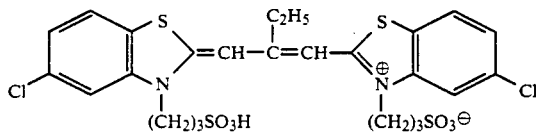

S-2

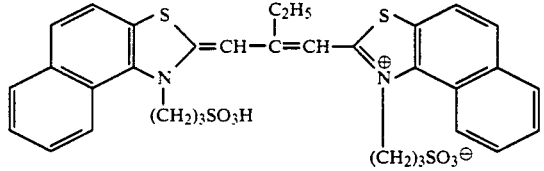

S-3

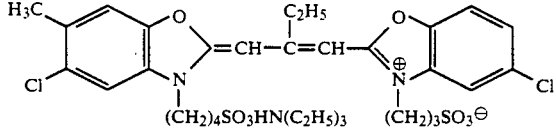

S-4

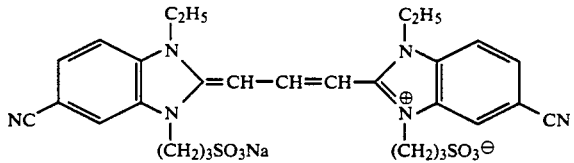

S-5

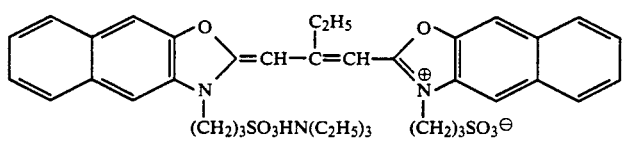

S-6

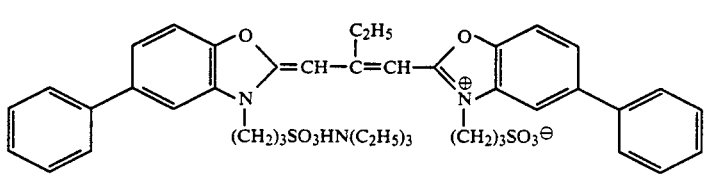

S-7

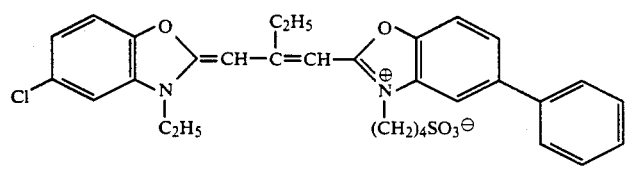
S-8
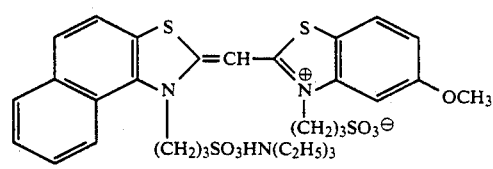
S-9
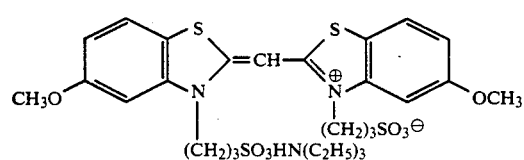
S-10
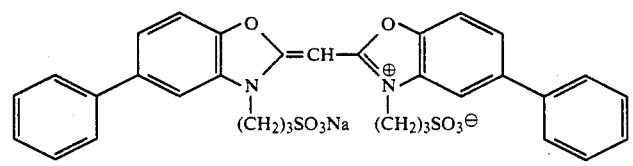
S-11
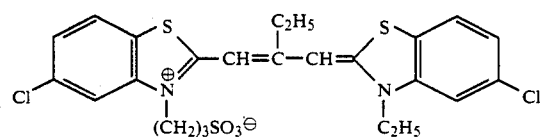
S-12
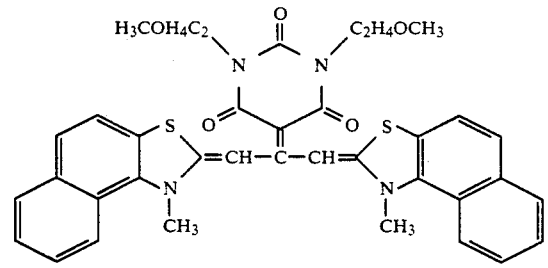
S-13
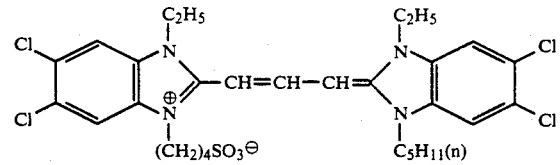
S-14
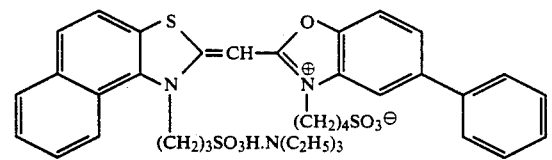
S-15
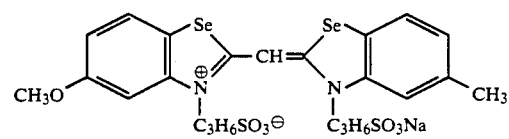
S-16

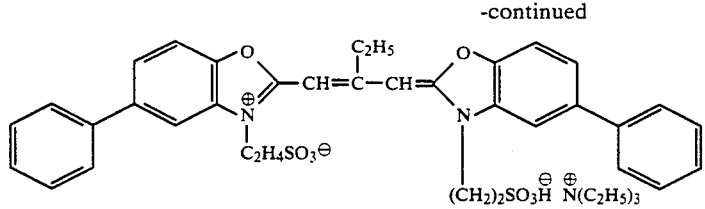
S-17
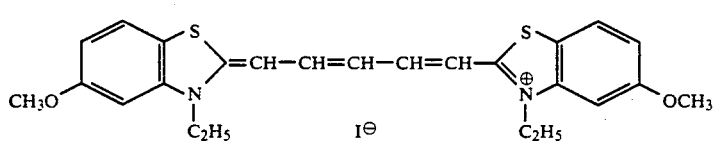
S-18
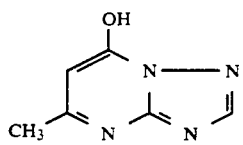
STB-1
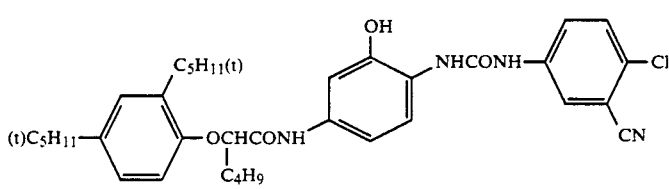
C-1
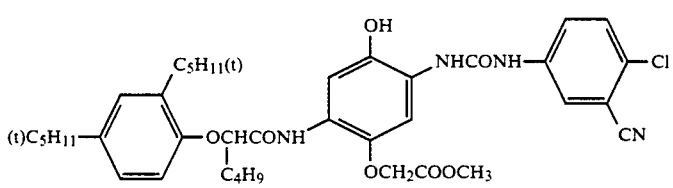
C-2
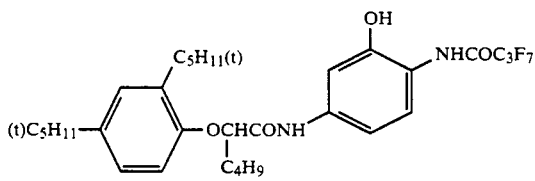
C-3
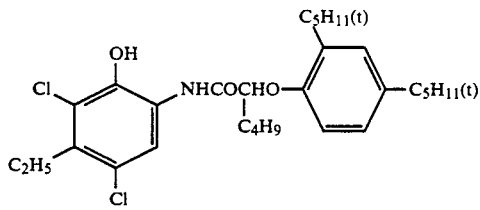
C-4
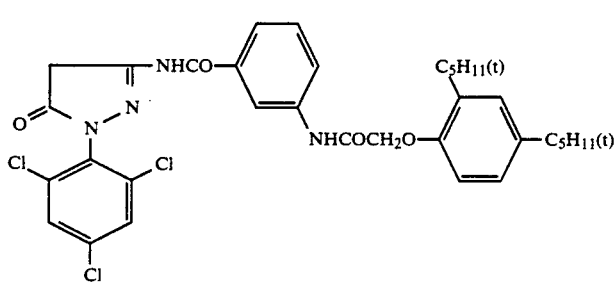
M-1

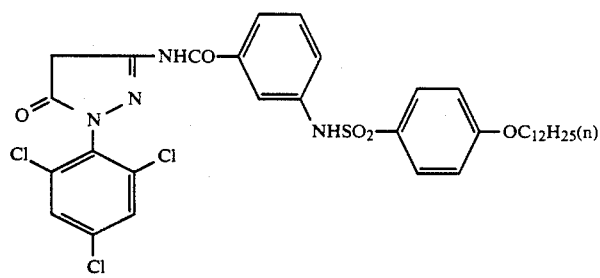
M-2
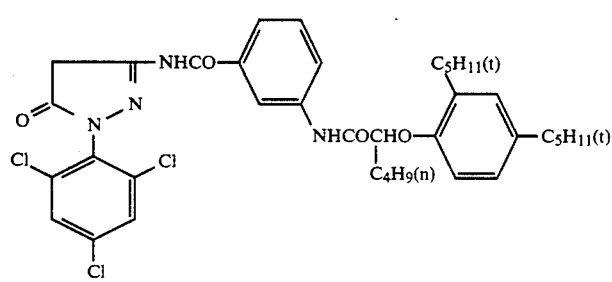
M-3
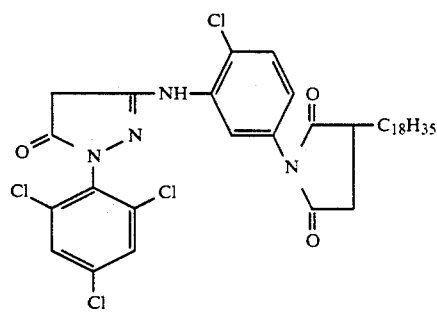
M-4
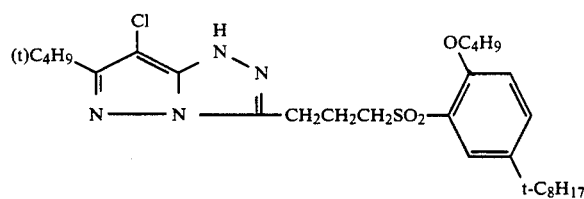
M-5
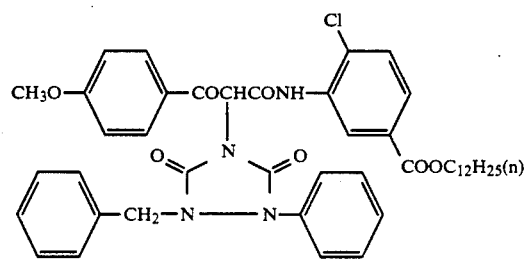
Y-1

-continued
Y-2
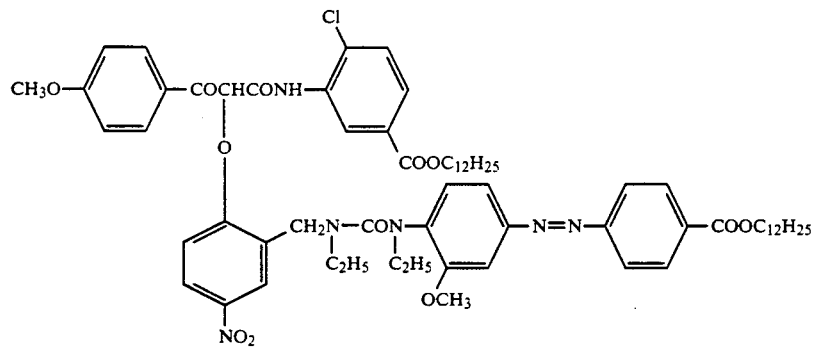
Y-3
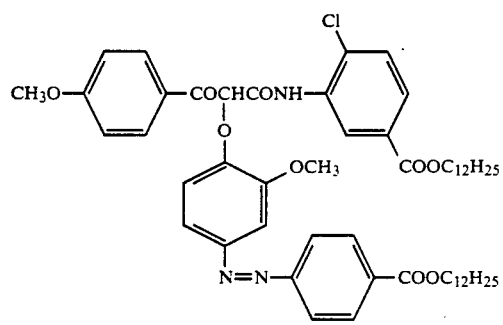
Y-4
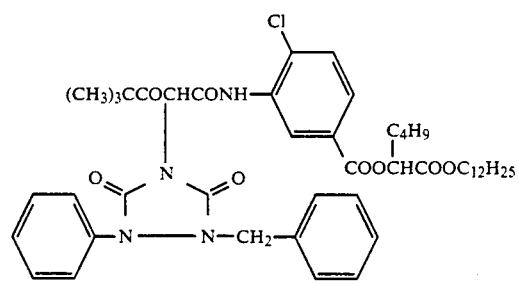
Y-5
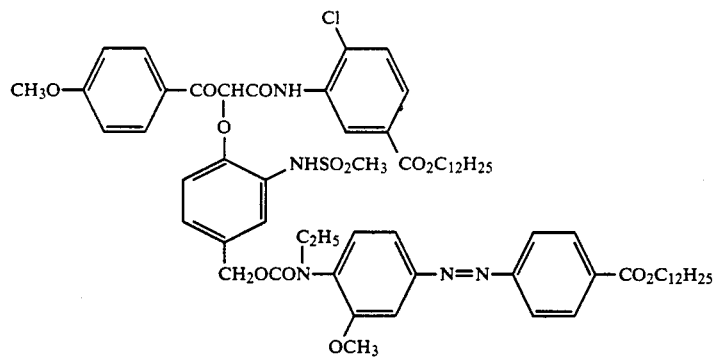
Y-6
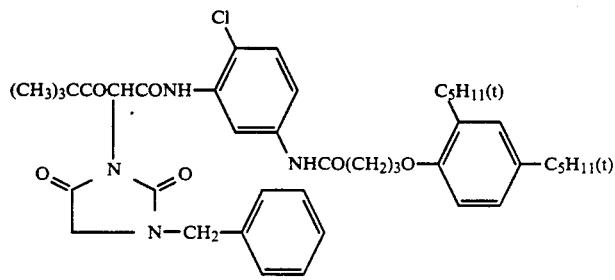

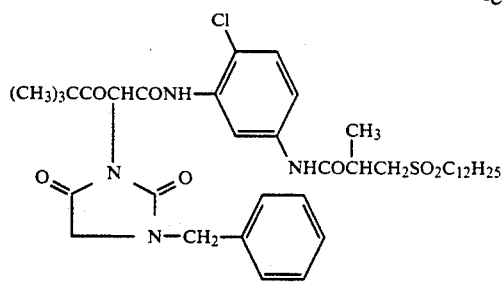
Y-7
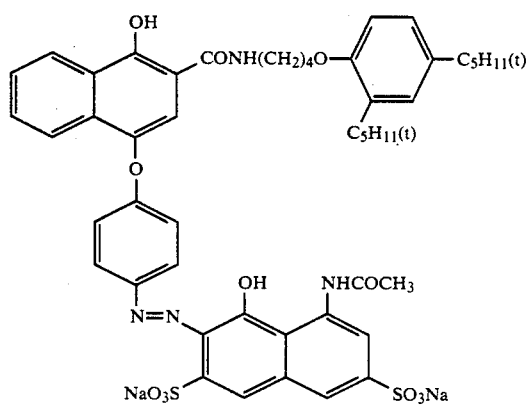
CC-1
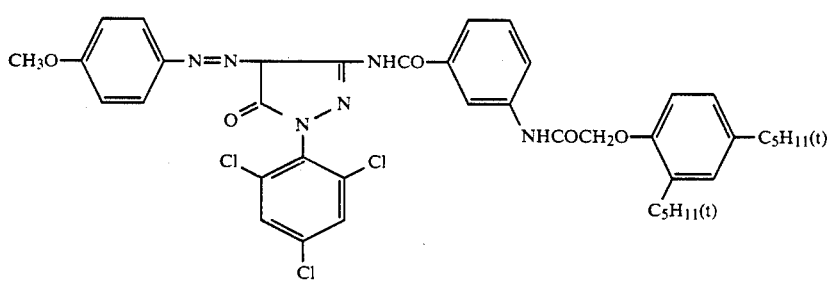
CM-1
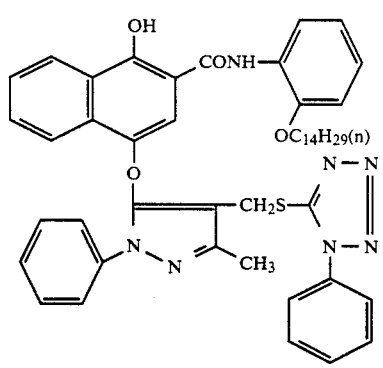
D-1
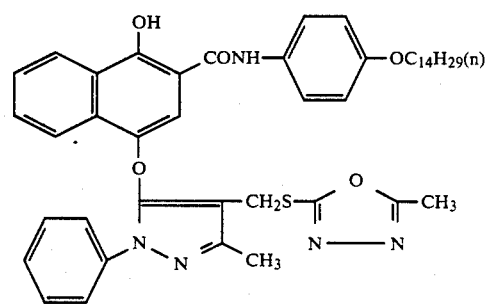
D-2

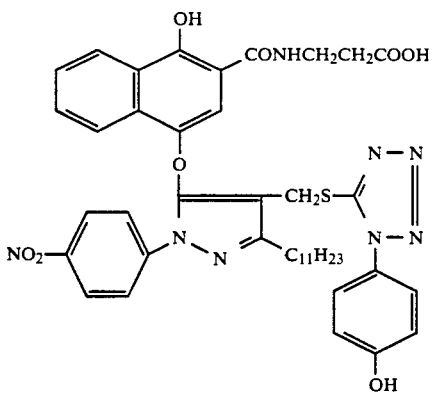
D-3
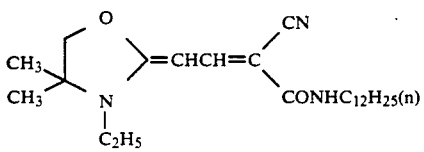
UV-1
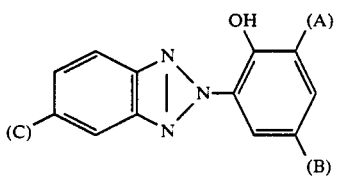
| A | B | C | |
|---|---|---|---|
| —H | —C₄H₉(t) | —H | UV-2 |
| —C₄H₉(t) | —C₄H₉(t) | —H | UV-3 |
| —C₄H₉(t) | —CH₃ | —Cl | UV-4 |
| —C₄H₉(t) | —C₄H₉(t) | —Cl | UV-5 |
| —C₄H₉(t) | —C₅H₁₁(t) | —H | UV-6 |
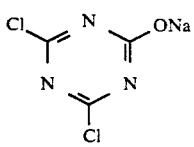
H-1
[(CH₂=CHSO₂CH₂)₃CCH₂SO₂(CH₂)₂]₂N(CH₂)₂SO₃K      H-2
(CH₂=CH—SO₂CH₂)₂O      H-3
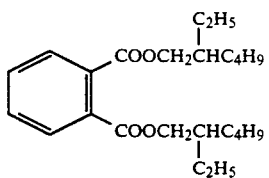
O-1
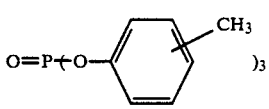
O-2
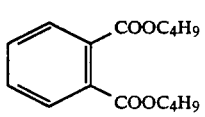
O-3
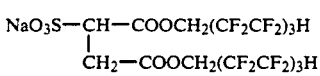
SU-1

-continued
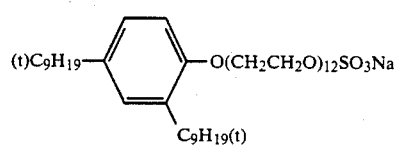 SU-2
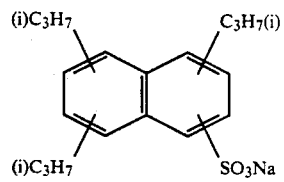 SU-3
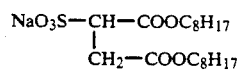 SU-4
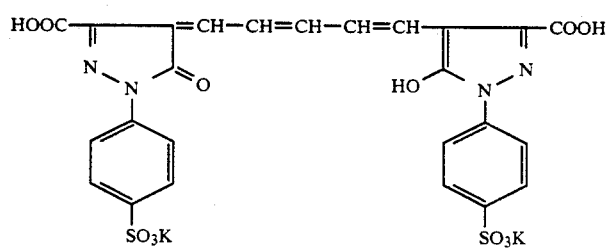 AI-1
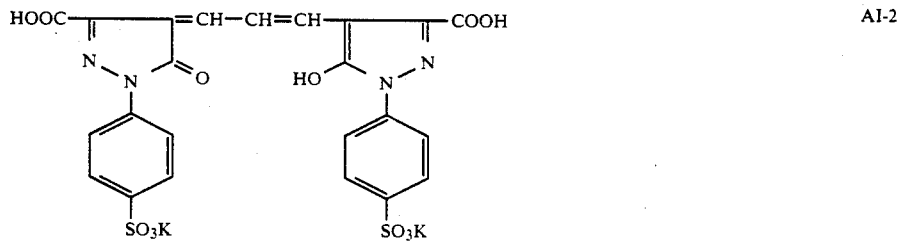 AI-2
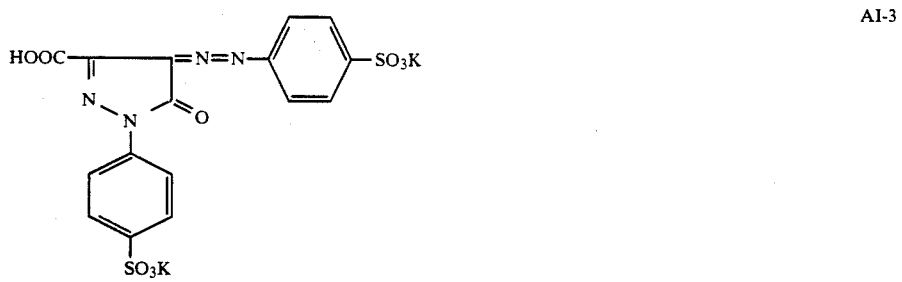 AI-3
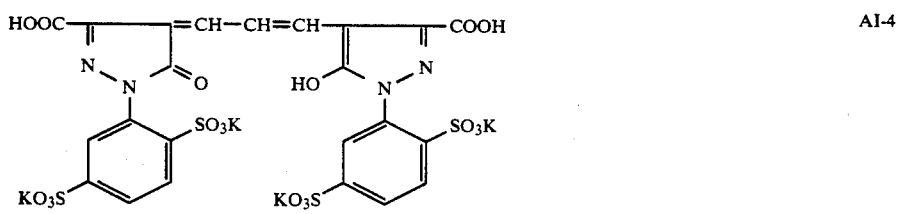 AI-4
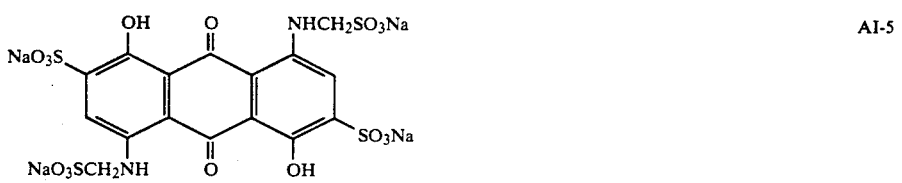 AI-5

-continued
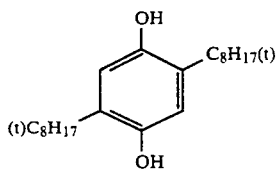 HQ-1
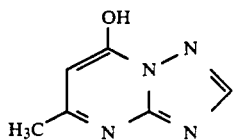 ST-1
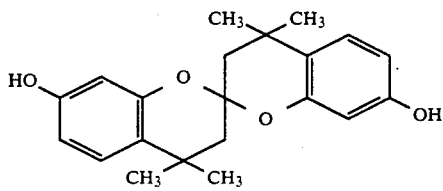 ST-2
Mixture of
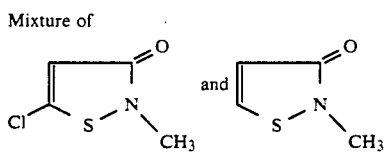 DI-1
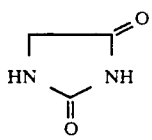 HS-1
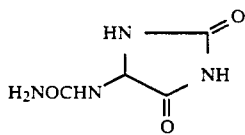 HS-2
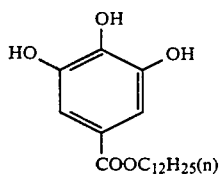 SC-1
Mixture (2:3) of
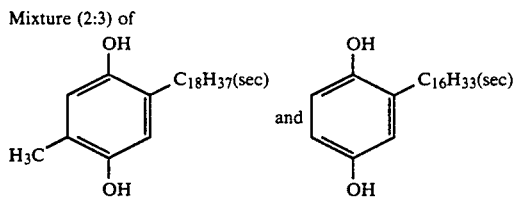 SC-2
Colloidal silica particles (average particle size: 3.5 μm)    MA-1
Polymethyl methacrylate particles (average particle size: 3.0 μm)    MA-2
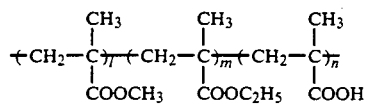 MA-2
(l:m:n = 30:30:40)

-continued

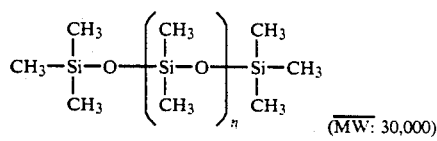

WAX-1

AF-1

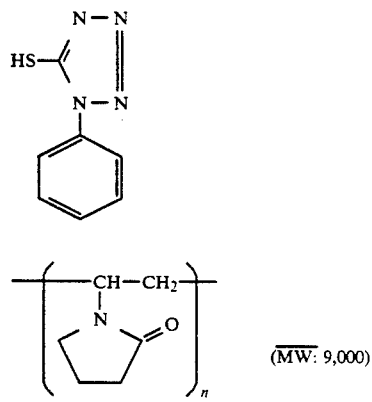

AF-2

Dy-1

Dy-2

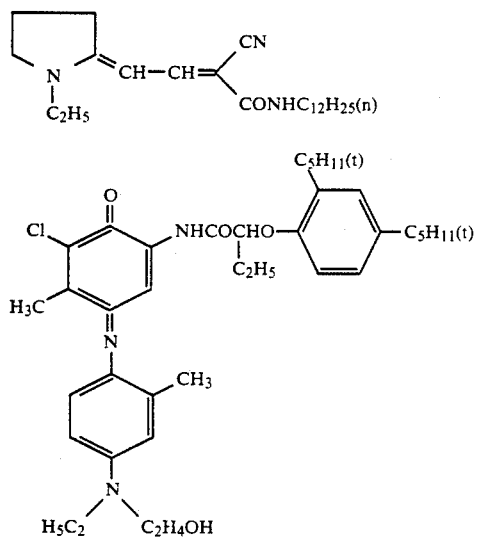

EXAMPLE 1

Preparation of comparative sample 101:

Tricresyl phosphate (3 g) was added to 6 g of a comparative yellow coupler (Y-1) and 18 g of ethyl acetate was added to the mixture, which was then heated at 60° C. to make a solution. The solution was mixed with 100 ml of a 5% aqueous gelatin solution containing 10 ml of a 5% aqueous solution of Alkanol B (the trade name of Du Pont for an alkylnaphthalenesulfonate). The mixture was sonicated to prepare a dispersion.

The dispersion was added to a AgBrI emulsion (6 mol % AgI) in such an amount that the yellow coupler comprised 10 mol % per mole of silver. Further, 1,2-bis(vinylsulfonyl)ethane was added as a hardener in an amount of 12 mg per gram of gelatin. The resulting coating solution was applied onto a subbed transparent triacetyl cellulose film base to give a silver deposit of 1.8 gm/cm$^2$. The so prepared photographic material was designated sample 101. Preparation of comparative samples 102 and 103 and samples 104-106 of the present invention:

Samples 102 to 106 were prepared by repeating the procedure for the preparation of sample 101 except that the yellow coupler (Y-1) was changed to the couplers shown in Table 1.

Samples 101-106 were exposed to light through an optical wedge and subsequently processed photographically by the following scheme.

| Step (38° C.) | Time |
| --- | --- |
| Color development | 3 min and 15 sec |
| Bleaching | 6 min and 30 sec |
| Washing | 3 min and 15 sec |
| Fixing | 6 min and 30 sec |
| Washing | 3 min and 15 sec |
| Stabilizing | 1 min and 30 sec |
| Drying | |

The processing solutions used in the steps of color development, bleaching, fixing and stabilization had the following compositions.

Color developing solution

| | |
|---|---|
| 4-Amino-3-methyl-N-ethyl-N(β-methyl-sulfonylaminoethyl)-aniline 3/2 sulfate (monohydrate) | 5.00 g |
| Anhydrous sodium sulfite | 4.25 g |
| Hydroxylamine hemisulfate | 2.0 g |
| Anhydrous potassium carbonate | 37.5 g |
| Sodium bromide | 1.3 g |
| Nitrilotriacetic acid 3Na salt (mono hydrate) | 2.5 g |
| Potassium hydroxide | 1.0 g |
| Water | to make 1,000 ml |
| pH | adjusted to 10.0 with KOH |
| Bleaching solution | |
| Ethylenediaminetetraacetic acid iron (III) ammonium salt | 100 g |
| Ethylenediaminetetraacetic acid ammonium salt | 10.0 g |
| Ammonium bromide | 150.0 g |
| Glacial acetic acid | 10.0 ml |
| Water | to make 1,000 ml |
| pH | adjusted to 6.0 with aqueous ammonia |
| Fixing solution | |
| Ammonium thiosulfate (50% aq. sol.) | 162 ml |
| Anhydrous sodium sulfite | 12.4 g |
| Water | to make 1,000 ml |
| pH | adjusted to 6.5 with acetic acid |
| Stabilizing solution | |
| Formaldehyde (37% aq. sol.) | 1.5 ml |
| Konidax (product of Konica Corp.) | 7.5 ml |
| Water | to make 1,000 ml |

The yellow dye images produced on the processed samples were evaluated for sensitivity (S1) and maximum density (Dmax). Sensitivity (S1) was expressed in terms of relative values, with the sensitivity of sample 101 being taken as 100. The results are shown in Table 1.

TABLE 1

| Sample | Coupler | S1 | Dmax | DoB |
|---|---|---|---|---|
| Comparison | | | | |
| 101 | Y-1 | 100 | 2.04 | 0.07 |
| 102 | Y-2 | 118 | 3.20 | 0.18 |
| 103 | Y-3 | 105 | 2.26 | 0.20 |
| Invention | | | | |
| 104 | exemplary compound (16) | 145 | 3.40 | 0.07 |
| 105 | exemplary compound (1) | 130 | 3.33 | 0.08 |
| 106 | exemplary compound (10) | 135 | 3.25 | 0.07 |

As is clear from Table 1, the couplers of the present invention had a higher sensitivity and were capable of more efficient color formation than comparative coupler Y-1. Compared to couplers Y-2 and Y-3, the couplers of the present invention were characterized by their being not colored. As a result, they did not cause color contamination of the blue region which was observed with comparative couplers Y-2 and Y-3.

EXAMPLE 2

Preparation of comparative sample 201:

A comparative sample (201) of multi-layered color photographic material was prepared by forming the following layers in the order written on a triacetyl cellulose film base.

In all examples that follow, the amounts of components or additives in silver halide photographic materials are expressed in grams per square meter unless otherwise noted. The amounts of silver halides and colloidal silver are calculated for silver. The amounts of spectral sensitizers are expressed in moles per mole of silver.

| Sample 101 (Comparison) | |
|---|---|
| First layer: Antihalation layer (HC) | |
| Black colloidal silver | 0.15 |
| UV absorber (UV-2) | 0.20 |
| Colored cyan coupler (CC-1) | 0.02 |
| High-boiling solvent (O-1) | 0.20 |
| High-boiling solvent (O-2) | 0.20 |
| Gelatin | 1.6 |
| Second layer: Intermediate layer (IL-1) | |
| Gelatin | 1.3 |
| Third layer: Less red-sensitive emulsion layer (R-L) | |
| Silver iodobromide emulsion (Em-1) | 0.4 |
| Silver iodobromide emulsion (Em-2) | 0.3 |
| Spectral sensitizer (S-1) | $3.1 \times 10^{-4}$ |
| Spectral sensitizer (S-2) | $3.2 \times 10^{-4}$ |
| Spectral sensitizer (S-3) | $0.2 \times 10^{-4}$ |
| Cyan coupler (C-1) | 0.50 |
| Cyan coupler (C-2) | 0.13 |
| Colored cyan coupler (CC-1) | 0.07 |
| DIR compound (D-1) | 0.006 |
| DIR compound (D-2) | 0.01 |
| High-boiling solvent (O-1) | 0.55 |
| Additive (SC-1) | 0.003 |
| Gelatin | 1.0 |
| Fourth layer: Highly red-sensitive emulsion layer (R-H) | |
| Silver iodobromide emulsion (Em-3) | 0.9 |
| Spectral sensitizer (S-1) | $1.7 \times 10^{-4}$ |
| Spectral sensitizer (S-2) | $1.6 \times 10^{-4}$ |
| Spectral sensitizer (S-3) | $0.1 \times 10^{-4}$ |
| Cyan coupler (C-2) | 0.23 |
| Colored cyan coupler (CC-1) | 0.03 |
| DIR compound (D-2) | 0.02 |
| High boiling solvent (O-1) | 0.25 |
| Additive (SC-1) | 0.003 |
| Gelatin | 1.0 |
| Fifth layer: Intermediate layer (IL-2) | |
| Gelatin | 0.8 |
| Sixth layer: Less green-sensitive emulsion layer (G-L) | |
| Silver iodobromide emulsion (Em-1) | 0.6 |
| Silver iodobromide emulsion (Em-2) | 0.2 |
| Spectral sensitizer (S-4) | $6.7 \times 10^{-4}$ |
| Spectral sensitizer (S-5) | $0.8 \times 10^{-4}$ |
| Magenta coupler (M-1) | 0.17 |
| Magenta coupler (M-2) | 0.43 |
| Colored magenta coupler (CM-1) | 0.10 |
| DIR compound (D-3) | 0.02 |
| High-boiling solvent (O-2) | 0.70 |
| Additive (SC-1) | 0.003 |
| Gelatin | 1.0 |
| Seventh layer: Highly green-sensitive emulsion layer (G-H) | |
| Silver iodobromide emulsion (Em-3) | 0.9 |
| Spectral sensitizer (S-6) | $1.1 \times 10^{-4}$ |
| Spectral sensitizer (S-7) | $2.0 \times 10^{-4}$ |
| Spectral sensitizer (S-8) | $0.3 \times 10^{-4}$ |
| Magenta coupler (M-1) | 0.03 |
| Magenta coupler (M-2) | 0.13 |
| Colored magenta coupler (CM-1) | 0.04 |
| DIR compound (D-3) | 0.004 |
| High-boiling solvent (O-2) | 0.35 |
| Additive (SC-1) | 0.003 |
| Gelatin | 1.0 |
| Eighth layer: Yellow filter layer (YC) | |
| Yellow colloidal silver | 0.1 |
| Additive (HS-1) | 0.07 |
| Additive (HS-2) | 0.07 |
| Additive (SC-2) | 0.12 |
| High-boiling solvent (O-2) | 0.15 |
| Gelatin | 1.0 |
| Ninth layer: Less blue-sensitive emulsion layer (B-L) | |
| Silver iodobromide emulsion (Em-1) | 0.25 |

-continued

| Sample 101 (Comparison) | |
|---|---|
| Silver iodobromide emulsion (Em-2) | 0.25 |
| Spectral sensitizer (S-9) | $5.8 \times 10^{-4}$ |
| Yellow coupler (Y-1) | 0.92 |
| DIR compound (D-1) | 0.003 |
| DIR compound (D-2) | 0.006 |
| High-boiling solvent (O-2) | 0.18 |
| Additive (SC-1) | 0.004 |
| Gelatin | 1.3 |
| Tenth layer: Highly blue-sensitive emulsion layer (B-H) | |
| Silver iodobromide (Em-4) | 0.5 |
| Spectral sensitizer (S-10) | $3.0 \times 10^{-4}$ |
| Spectral sensitizer (S-11) | $1.2 \times 10^{-4}$ |
| Yellow coupler (Y-1) | 0.28 |
| High-boiling solvent (O-2) | 0.05 |
| Additive (SC-1) | 0.002 |
| Gelatin | 1.0 |
| Eleventh layer: First protective layer (PRO-1) | |
| Silver iodobromide (Em-5) | 0.3 |
| UV absorber (UV-1) | 0.1 |
| UV absorber (UV-2) | 0.07 |
| Additive (HS-1) | 0.2 |
| Additive (HS-2) | 0.1 |
| High-boiling solvent (O-1) | 0.07 |
| High-boiling solvent (O-3) | 0.07 |
| Gelatin | 0.8 |
| Twelfth layer: Second protective layer (PRO-2) | |
| Alakli-soluble matting agent (average particle size, 2 μm) | 0.13 |
| Polymethyl methacrylate (average particle size, 3 μm) | 0.02 |
| Slip agent (WAX-1) | 0.04 |
| Charge control agent (SU-1) | 0.004 |
| Charge control agent (SU-2) | 0.02 |
| Gelatin | 0.5 |

The yellow coupler (Y-1) in each of the ninth and tenth layers was used in an experimentally determined amount that would provide a Dmax of ca. 2.5 after exposure.

Besides the compounds mentioned above, a coating aid (SU-4), a dispersion aid (SU-3), hardeners (H-1) and (H-2), a stabilizer (ST-1), an antiseptic (DI-1), antifoggants (AF-1) and (AF-2), and dyes (AI-1) and (AI-2) were also added as appropriate.

The emulsions used in sample 201 are identified below. All of them are monodispersed emulsions having a higher iodine content in the interior of grains than on their surface.

Em-1: 7.5 mol % AgI on average; ocrahedral; 0.55 μm
Em-2: 2.5 mol % AgI on average; octahedral; 0.36 μm
Em-3: 8.0 mol % AgI on average; octahedral; 0.84 μm
Em-4: 8.5 mol % AgI on average; octahedral; 1.02 μm
Em-5: 2.0 mol % AgI on average; 0.08 μm Preparation of comparative samples 202 and 203 and samples 204–209 of the present invention:

Samples 202–209 were prepared by repeating the procedure for the preparation of sample 201 except for the following points: the yellow coupler Y-1 in the ninth and tenth layers of sample 201 was changed to the couplers shown in Table 2; the amounts of the substituting couplers were changed to those which would provide a Dmax of ca. 2.5 after exposure; and the amounts of high-boiling organic solvent (O-2) and gelatin were adjusted accordingly.

Samples 201–209 were given exposure for MTF measurements and subsequently processed photographically by the following scheme.

| Step (38° C.) | Time |
|---|---|
| Color development | 3 min and 15 sec |
| Bleaching | 6 min and 30 sec |
| Washing | 3 min and 15 sec |
| Fixing | 6 min and 30 sec |
| Washing | 3 min and 15 sec |
| Stabilizing | 1 min and 30 sec |
| Drying | |

The processing solutions used in the color developing, bleaching and fixing steps had the following compositions.

| Color developing solution | |
|---|---|
| 4-Amino-3-methyl-N-ethyl-N-(β-hydroxyethyl)aniline sulfate | 4.75 g |
| Anhydrous sodium sulfite | 4.25 g |
| Hydroxylamine hemisulfate | 2.0 g |
| Anhydrous calcium carbonate | 37.5 g |
| Sodium bromide | 1.3 g |
| Nitrilotriacetic acid trisodium salt (monohydrate) | 2.5 g |
| Potassium hydroxide | 1.0 g |
| Water | to make 1,000 ml |
| pH | adjusted to 10.0 with KOH |
| Bleaching solution | |
| Ethylenediaminetetraacetic acid iron (III) ammonium salt | 100 g |
| Ethylenediaminetetraacetic acid ammonium salt | 10.0 g |
| Ammonium bromide | 150.0 g |
| Glacial acetic acid | 10 ml |
| Water | to make 1,000 ml |
| pH | adjusted to 6.0 with aqueous ammonia |
| Fixing solution | |
| Ammonium thiosulfate (50% aq. sol.) | 162 ml |
| Anhydrous sodium sulfite | 12.4 g |
| Water | to make 1,000 ml |
| pH | adjusted to 6.5 with acetic acid |

The measured MTF values are shown in Table 2. MTF values were determined for cyan image by the method described in T. H. James, "The Theory of the Photographic Process", Fourth Edition, p. 605, Macmillan Publishing Company, 1977.

TABLE 2

| Sample | Coupler | Dmax | MTF (40 lines/mm) |
|---|---|---|---|
| Comparison | | | |
| 201 | Y-1 | 2.52 | 0.34 |
| 202 | Y-2 | 2.51 | 0.38 |
| 203 | Y-3 | 2.48 | 0.37 |
| Invention | | | |
| 204 | exemplary compound (9) | 2.51 | 0.45 |
| 205 | exemplary compound (14) | 2.50 | 0.43 |
| 206 | exemplary compound (15) | 2.50 | 0.44 |
| 207 | exemplary compound (16) | 2.49 | 0.45 |
| 208 | exemplary compound (31) | 2.49 | 0.42 |
| 209 | exemplary compound (34) | 2.48 | 0.42 |

The data in Table 2 shows that the samples prepared using the couplers of the present invention produced cyan image of improved sharpness. This would be explained as follows: those samples permitted yellow couplers to be used in smaller amounts for attaining the same level of Dmax and the necessary amounts of high-boiling solvents and gelatin could accordingly be reduced; as a result, the thickness of yellow dye-forming layers could be sufficiently reduced to cause less scattering of incident light, thereby improving the sharpness of cyan image that could be produced.

EXAMPLE 3

Preparation of sample 301:

A comparative sample (301) of multi-layered color photographic material was prepared by coating the following layers in the order written on a subbed cellulose triacetate film base.

| First layer: Antihalation layer | |
|---|---|
| Black colloidal silver | 0.24 |
| UV absorber (UV-2) | 0.14 |
| UV absorber (UV-3) | 0.072 |
| UV absorber (UV-4) | 0.072 |
| UV absorber (UV-5) | 0.072 |
| High-boiling solvent (O-1) | 0.31 |
| High-boiling solvent (O-3) | 0.098 |
| Poly-N-vinylpyrrolidone | 0.15 |
| Gelatin | 2.02 |
| Second layer: Intermediate layer | |
| Dye (D-1) | 0.011 |
| High-boiling solvent (O-2) | 0.011 |
| Gelatin | 1.17 |
| Third layer: Less red-sensitive layer | |
| AgBrI emulsion (3.0 mol % AgI; 0.57 μm) spectrally sensitized with red spectral sensitizers S-12 and S-13 | 0.056 |
| AgBrI emulsion (3.0 mol % AgI; 0.27 μm) spectrally sensitized with red spectral sensitizers S-12 and S-13 | 0.504 |
| Coupler (C-4) | 0.37 |
| High-boiling solvent (O-3) | 0.093 |
| Poly-N-vinylpyrrolidone | 0.074 |
| Gelatin | 1.35 |
| Fourth layer: Highly red-sensitive layer | |
| AgBrI emulsion (3.0 mol % AgI; 0.57 μm) spectrally sensitized with red spectral sensitizers S-12 and S-13 | 0.71 |
| Coupler (C-4) | 0.85 |
| High-boiling solvent (O-3) | 0.21 |
| Poly-N-vinylpyrrolidone | 0.093 |
| Gelatin | 1.56 |
| Fifth layer: intermediate layer | |
| Antistain agent (SC-1) | 0.20 |
| High-boiling solvent (O-2) | 0.25 |
| Matting agent (MA-1) | 0.0091 |
| Gelatin | 1.35 |
| Sixth layer: Less green-sensitive layer | |
| AgBrI emulsion (3.0 mol % AgI; 0.60 μm) spectrally sensitized with green spectral sensitizers S-2 and S-14 | 0.056 |
| AgBrI emulsion (3.0 mol % AgI; 0.27 μm) spectrally sensitized with green spectral sensitizers S-2 and S-14 | 0.51 |
| Coupler (M-1) | 0.31 |
| Coupler (M-3) | 0.076 |
| High-boiling solvent (O-2) | 0.059 |
| Poly-N-vinylpyrrolidone | 0.074 |
| Gelatin | 1.29 |
| Seventh layer: Highly green-sensitive layer | |
| AgBrI emulsion (3.0 mol % AgI; 0.60 μm) spectrally sensitized with green spectral sensitizers S-2 and S-14 | 0.83 |
| AgBrI emulsion (3.0 mol % AgI; 0.27 μm) spectrally sensitized with green spectral sensitizers S-2 and S-14 | 0.092 |
| Coupler (M-1) | 0.80 |
| Coupler (M-3) | 0.19 |
| Antistain agent (SC-1) | 0.055 |
| High-boiling solvent (O-2) | 0.16 |
| Poly-N-vinylpyrrolidone | 0.12 |

| -continued | |
|---|---|
| Gelatin | 1.91 |
| Eighth layer: Intermediate layer | |
| Gelatin | 0.90 |
| Ninth layer: Yellow filter layer | |
| Yellow colloidal silver | 0.11 |
| Antistain agent (SC-1) | 0.068 |
| High-boiling solvent (O-2) | 0.085 |
| Matting agent (MA-1) | 0.012 |
| Gelatin | 0.68 |
| Tenth layer: Less blue-sensitive layer | |
| AgBrI emulsion (3.0 mol % AgI; 0.85 μm) spectrally sensitized with blue spectral sensitizers S-11 and S-15 | 0.24 |
| AgBrI emulsion (3.0 mol % AgI; 0.42 μm) spectrally sensitized with blue spectral sensitizers S-11 and S-15 | 0.30 |
| AgBrI emulsion (3.0 mol % AgI; 0.27 μm) spectrally senstized with blue spectral sensitizers S-11 and S-15 | 0.060 |
| Coupler (Y-4) | 0.86 |
| Image stabilizer (SC-1) | 0.012 |
| High-boiling solvent (O-2) | 0.22 |
| Poly-N-vinylpyrrolidone | 0.078 |
| Compound (HS-2) | 0.020 |
| Compound (HS-1) | 0.040 |
| Gelatin | 1.50 |
| Eleventh layer: Highly blue-sensitive layer | |
| AgBrI emulsion (3.0 mol % AgI; 0.85 μm) spectrally sensitized with blue spectral sensitizers S-11 and S-15 | 0.79 |
| Coupler (Y-4) | 1.24 |
| Image stabilizer (SC-1) | 0.017 |
| High boiling solvent (O-2) | 0.31 |
| Poly-N-vinylpyrrolidone | 0.10 |
| Compound (HS-2) | 0.039 |
| Compound (HS-1) | 0.077 |
| Gelatin | 1.73 |
| Twelfth layer: Protective layer - 1 | |
| Non-light-sensitive fine particulate AgBrI (1.0 mol % AgI; 0.08 μm) | 0.075 |
| UV absorber UV-2 | 0.048 |
| UV absorber UV-3 | 0.024 |
| UV absorber UV-4 | 0.024 |
| UV absorber UV-5 | 0.024 |
| Dye (Dy-1) | 0.064 |
| UV-1 | 0.13 |
| High-boiling solvent (O-1) | 0.13 |
| High boiling solvent (O-3) | 0.13 |
| Compound (HS-2) | 0.075 |
| Compound (HS-1) | 0.15 |
| Gelatin | 1.2 |
| Thirteenth layer: Protective layer - 2 | |
| Slip agent (WAX-1) | 0.041 |
| Matting agent (MA-2) | 0.0090 |
| Matting agent (MA-3) | 0.051 |
| Surfactant SU-1 | 0.0036 |
| Gelatin | 0.55 |

(Note: Poly-N-vinylpyrrolidone used in layers 1, 3, 4, 6, 7, 10 and 11 had an average molecular weight of 350,000.)

Besides the compounds mentioned above, gelatin hardeners H-1, H-2 and H-3, water-soluble dyes AI-1, AI-2 and A-3, mold inhibitor DI-1, stabilizer ST-1 and antifoggant AF-1 were added as appropriate.

Preparation of comparative sample 302 and samples 303-305 of the present invention:

Samples 302-305 were prepared by repeating the procedure for the preparation of sample 301 except for the following points: the yellow coupler Y-4 in the tenth and eleventh layers of sample 301 were changed to the couplers (55%) shown in Table 3; the amounts of high-boiling organic solvent (O-2) and gelatin were reduced accordingly.

Samples 301-305 were exposed to light through an optical wedge and subsequently processed photographically by the following scheme.

| Step | Time, min | Temperature, °C. |
|---|---|---|
| First development | 6 | 38 |
| Washing | 2 | 38 |
| Reversal | 2 | 38 |
| Color development | 6 | 38 |
| Adjustment | 2 | 38 |
| Bleaching | 6 | 38 |
| Fixing | 4 | 38 |
| Washing | 4 | 38 |
| Stabilizing | 1 | R.T. |
| Drying | | |

The processing solutions used in the steps other than washing and drying had the following compositions.

| First developing solution | |
|---|---|
| Sodium tetrapolyphosphate | 2 g |
| Sodium sulfite | 20 g |
| Hydroquinone monosulfonate | 30 g |
| Sodium carbonate (monohydrate) | 30 g |
| 1-Phenyl-4-methyl-4-hydroxymethyl-3-pyrazolidone | 2 g |
| Potassium bromide | 2.5 g |
| Potassium thiocyante | 1.2 g |
| Potassium iodide (0.1% aq. sol.) | 2 ml |
| Water | to make 1,000 ml |
| pH | 9.60 |
| Reversal solution | |
| Nitrilotrimethylenephosphonic acid Hexasodium salt | 3 g |
| Stannous chloride ($2H_2O$) | 1 g |
| p-Aminophenol | 0.1 g |
| Sodium hydroxide | 8 g |
| Glacial acetic acid | 15 ml |
| Water | to make 1,000 ml |
| pH | 5.75 |
| Color developing solution | |
| Sodium tetrapolyphosphate | 3 g |
| Sodium sulfite | 7 g |
| Sodium tertiary phosphate ($2H_2O$) | 36 g |
| Potassium bromide | 1 g |
| Potassium iodide (0.1% aq. sol.) | 90 ml |
| Sodium hydroxide | 3 g |
| Citrazinic acid | 1.5 g |
| N-Ethyl-N-$\beta$-methanesulfonamidoethyl-3-methyl-4-aminoaniline sulfate | 11 g |
| 2,2-Ethylenedithiodiethanol | 1 g |
| Water | to make 1,000 ml |
| pH | 11.70 |
| Adjusting solution | |
| Sodium sulfite | 12 g |
| Ethylenediaminetetraacetic acid sodium salt ($2H_2O$) | 8 g |
| Thioglycerin | 0.4 ml |
| Glacial acetic acid | 3 ml |
| Water | to make 1,000 ml |
| pH | 6.15 |
| Bleaching solution | |
| Ethylenediaminetetraacetic acid sodium salt ($2H_2O$) | 2 g |
| Ethylenediaminetetraacetic acid iron (III) ammonium salt ($2H_2O$) | 120 g |
| Ammonium bromide | 100 g |
| Water | to make 1,000 ml |
| pH | 5.65 |
| Fixing solution | |
| Ammonium thiosulfate | 80 g |
| Sodium sulfite | 5 g |
| Sodium bisulfite | 5 g |
| Water | to make 1,000 ml |
| pH | 6.60 |
| Stabilizing solution | |
| Formaldehyde (37 wt % aq. sol.) | 5 ml |
| Konidax (product of Konica Corp.) | 5 ml |
| Water | to make 1,000 ml |

The processed samples were evaluated for the maximum density (Dmax) of yellow dye image and the MTF value of cyan image.

In another run, samples 301–305 were not developed but immediately subjected to bleaching, fixing and subsequent steps. Blue density (DoB) was measured for each of these processed samples.

The results are shown in Table 3.

TABLE 3

| Sample | Coupler | Dmax | DoB | MTF (40 lines/mm) |
|---|---|---|---|---|
| Comparison | | | | |
| 301 | Y-4 | 3.20 | 0.10 | 0.37 |
| 302 | Y-5 | 2.69 | 0.22 | 0.43 |
| Invention | | | | |
| 303 | exemplary compound (10) | 3.18 | 0.10 | 0.46 |
| 304 | exemplary compound (16) | 3.21 | 0.10 | 0.49 |
| 305 | exemplary compound (20) | 3.17 | 0.09 | 0.48 |

As is clear from Table 3, the samples prepared using the couplers within the scope of the present invention exhibited excellent sharpness. Furthermore, compared to Y-5, those couplers were not colored and hence were found to be effectively used in light-sensitive materials for direct viewing.

EXAMPLE 4

Preparation of comparative sample 401:

A comparative sample (401) of multi-color silver halide photographic material was prepared by coating the following layers in the order written on a paper base laminted with polyethylene on both sides.

| First layer: Blue-sensitive silver halide emulsion layer | |
|---|---|
| Monodispersed emulsion comprising silver chloride grains ($\geq$99.5 mol % AgCl) | 3.2 mg/100 cm$^2$ (Ag deposit) |
| Yellow coupler (Y-6) | 6.8 mg/100 cm$^2$ |
| Dibutyl phthalate | 3.5 mg/100 cm$^2$ |
| Gelatin | 13.5 mg/100 cm$^2$ |
| Second layer: Intermediate layer | |
| HQ-1 | 0.5 mg/100 cm$^2$ |
| Dibutyl phthalate | 0.5 mg/100 cm$^2$ |
| Gelatin | 9.0 mg/100 cm$^2$ |
| Third layer: Green-sensitive silver halide emulsion layer | |
| Monodispersed emulsion comprising silver chloride grains ($\geq$99.5 mol % AgCl) | 2.5 mg/100 cm$^2$ (Ag deposit) |
| Magenta coupler (M-4) | 3.5 mg/100 cm$^2$ |
| Dibutyl phthalate | 3.0 mg/100 cm$^2$ |
| Gelatin | 12.0 mg/100 cm$^2$ |
| Fourth layer: Intermediate layer | |
| UV absorber (UV-3) | 7.0 mg/100 cm$^2$ |
| Dibutyl phthalate | 3.0 mg/100 cm$^2$ |
| HQ-1 | 0.5 mg/100 cm$^2$ |
| Gelatin | 12.0 mg/100 cm$^2$ |
| Fifth layer: Red-sensitive silver halide emulsion layer | |
| Monodispersed emulsion comprising AgBrCl grains (80 mol % agBr) | 3.0 mg/100 cm$^2$ (Ag deposit) |
| Cyan coupler (C-4) | 4.2 mg/100 cm$^2$ |
| Tricresyl phosphate | 3.5 mg/100 cm$^2$ |
| Gelatin | 11.5 mg/100 cm$^2$ |
| Sixth layer: Protective layer | |
| Gelatin | 8.0 mg/100 cm$^2$ |

Preparation of comparative sample 402 and samples 403 and 404 of the present invention:

Samples 402–404 were prepared by repeating the procedure for the preparation of sample 401 except for the following points: the yellow coupler (Y-6) in the first layer of sample 401 was changed to the couplers shown in Table 4; and the silver deposit on the first layer was reduced to 1.8 mg/100 cm$^2$.

The samples thus prepared were subjected to wedge exposure in the usual manner and subsequently processed by the following scheme using the processing solutions also shown below.

| Step | Temperature, °C. | Time, sec |
|---|---|---|
| Color development | 35.0 ± 0.3 | 45 |
| Bleach-fixing | 35.0 ± 0.5 | 45 |
| Stabilizing | 30–34 | 90 |
| Drying | air-dried at 25° C. | — |

| Color developing solution | |
|---|---|
| Pure water | 800 ml |
| Triethanolamine | 10 g |
| N,N-Diethylhydroxylamine | 5 g |
| Potassium bromide | 0.02 g |
| Potassium chloride | 2 g |
| Potassium sulfite | 0.3 g |
| 1-Hydroxyethylidene-1,1-diphosphonic acid | 1.0 g |
| Ethylenediaminetetraacetic acid | 1.0 g |
| Disodium catechol-3,5-disulfonate | 1.0 g |
| N-Ethyl-N-β0methanesulfonamido-ethyl-3-methyl-4-aminoaniline sulfate | 4.5 g |
| Optical brightening agent (4,4'-diaminostilbenedisulfonic acid derivative) | 10 g |
| Potassium carbonate | 27 g |
| Water | to make 1,000 ml |
| pH | adjusted to 10.10 |
| Bleach-fixing solution | |
| Ethylenediaminetetraacetic acid iron (III) ammonium dihydrate | 60 g |
| Ethylenediaminetetraacetic acid | 3 g |
| Ammonium thiosulfate (70% aq. sol.) | 100 ml |
| Ammonium sulfite (40% aq. sol.) | 27.5 ml |
| Water | to make 1,000 ml |
| pH | adjusted to 6.2 with potassium carbonate or glacial acetic acid |
| Stabilizing solution | |
| 5-Chloro-2-methyl-4-isothiazolin-3-one | 1.0 g |
| Ethyleneglycol | 1.0 g |
| 1-Hydroxyethylidene-1,1-diphosphonic acid | 2.0 g |
| Ethylenediaminetetraacetic acid | 1.0 g |
| Ammonium hydroxide (20% aq. sol.) | 3.0 g |
| Ammonium sulfite | 3.0 g |
| Optical brightening agent (4,4'-diaminostilbenediphosphonic acid derivative) | 1.5 g |
| Water | to make 1,000 ml |
| pH | adjusted to 7.0 with H$_2$SO$_4$ or KOH |

The dye images formed on the processed samples were measured for maximum color density and fog. At the same time, the sensitivity of each sample was measured. The results are shown in Table 4.

TABLE 4

| Sample | Ag deposit (mg/100 cm$^2$) | Coupler | Dmax | Fog | Sensitivity |
|---|---|---|---|---|---|
| Comparison | | | | | |
| 401 | 3.2 | Y-6 | 2.34 | 0.05 | 100 |
| 402 | 1.8 | Y-6 | 1.26 | 0.04 | 76 |
| 403 | 1.8 | Y-2 | 2.21 | 0.14 | 82 |
| Invention | | | | | |
| 404 | 1.8 | exemplary compound (8) | 2.33 | 0.05 | 120 |
| 405 | 1.8 | exemplary compound (20) | 2.35 | 0.04 | 123 |

As Table 4 shows, the samples prepared in accordance with the present invention had higher sensitivity and were capable of efficient color formation even when the amount of silver in emulsion layer was reduced.

EXAMPLE 5

Preparation of silver halide emulsions:

The three types of silver halide emulsion shown in Table 5 were prepared by a neutral and a double-jet method.

TABLE 5

| Emulsion | AgCl (mol %) | AgBr (mol %) | Average grain size, μ | Chemical sensitizer | Spectral sensitizer |
|---|---|---|---|---|---|
| Em-1 | 100 | 0 | 0.67 | sodium thiosulfate*[1] | S-16*[3] |
| Em-2 | 99.5 | 0.5 | 0.46 |  | S-17*[4] |
| Em-3 | 99.5 | 0.5 | 0.43 | chloroauric acid*[2] | S-18*[5] |

*[1] added 2 mg per mole of silver halide
*[2] added 5 × 10$^{-5}$ moles per mole of silver halide
*[3] added 0.9 mmol per mole of silver halide
*[4] added 0.7 mmol per mole of silver halide
*[5] added 0.2 mmol per mole of silver halide After chemical sensitization, STB-1 (see below) was added as an emulsion stabilizer to each silver halide emulsion in an amount of $5 \times 10^{-3}$ moles per mole of silver halide.

Preparation of samples of silver halide color photographic material:

Samples 501–504 of silver halide color photographic material were prepared by simultaneous coating of the following layers 1–7 in the order written on a paper base laminated with polyethylene on both sides (the amounts of addition based on square meter of the photographic material).

Layer 1 ... a layer containing gelatin (1.2 g), 0.29 g (based on silver, which applies to the following description) of a blue-sensitive silver halide emulsion (Em-1), and 0.3 g of DOP (dioctyl phthalate) having dissolved therein 1.0 mmol of yellow coupler (see Table 5) and 0.015 g of 2,5-dioctyl hydroquinone (HQ-1);

Layer 2 ... a layer containing gelatin (0.9 g) and 0.2 g of DOP having 0.04 g of HQ-1 dissolved therein;

Layer 3 ... a layer containing gelatin (1.4 g), 0.2 g of a green-sensitive silver halide emulsion (Em-2), 0.3 g of DOP having dissolved therein 0.50 g of a magenta coupler (M-5), 0.25 g of a photostabilizer (ST-2) and 0.01 g of HQ-1, and 6 mg of a filter dye (AI-4);

Layer 4 ... a layer containing gelatin (1.2 g) and 0.3 g of DNP (dinonyl phthalate) having 0.6 g of a uv absorber (UV-6) and 0.05 g of HQ-1 dissolved therein;

Layer 5 ... a layer containing gelatin (1.4 g), 0.20 g of a red-sensitive silver halide emulsion (Em-3), and 0.3 g of DOP having dissolved therein 0.54 g of a cyan coupler (C-4), 0.01 g of HQ-1 and 0.3 g of ST-1 dissolved therein;

Layer 6 ... a layer containing gelatin (1.1 g), 0.2 g of DOP having 0.2 g of UV-6 dissolved therein, and 5 mg of a filter dye (AI-5);

Layer 7 ... a layer containing gelatin (1.0 g) and 0.05 g of 2,4-dichloro-6-hydroxytriazine sodium.

The prepared samples were subjected to exposure through an optical wedge on a sensitometer Model KS-7 (Konica Corp.), subsequently processed by the following scheme, and measured for the maximum density (Dmax) of the blue-sensitive emulsion layer using an optical densitometer (Model PDA-65 of Konica Corp.)

The samples were also subjected to a fading test with a fade-O-meter for 14 days and their lightfastness was evaluated by determining the percentage of redidual dye image at an initial density of 1.0. The results are shown in Table 6.

| Step | Processing scheme | |
|---|---|---|
| | Temperature, °C. | Time, sec |
| Color development | 34.7 ± 0.3 | 45 |
| Bleach-fixing | 34.7 ± 0.5 | 50 |
| Stabilizing | 30–34 | 90 |
| Drying | 60–80 | 60 |
| Color developing solution | | |
| Pure water | | 800 ml |
| Triethanolamine | | 8 g |
| N,N-Diethylhydroxylamine | | 5 g |
| Potassium chloride | | 2 g |
| N-Ethyl-N-β-methanesulfonamidoethyl-3-methyl-4-aminoaniline sulfate | | 5 g |
| Sodium tetrapolyphosphate | | 2 g |
| Potassium carbonate | | 30 g |
| Potassium sulfite | | 0.2 g |
| Optical brightening agent (4,4'-diamino-stilbenedisulfonic acid derivative) | | 1 g |
| Pure water | | to make 1,000 ml |
| pH | | adjusted to 10.2 |
| Bleach-fixing solution | | |
| Ethylenediaminetetraacetic acid iron (III) ammonium dihydrate | | 60 g |
| Ethylenediaminetetraacetic acid | | 3 g |
| Ammonium thiosulfate (70% aq. sol.) | | 100 ml |
| Ammonium sulfite (40% aq. sol.) | | 27.5 ml |
| Water | | to make 1,000 ml |
| pH | | adjusted to 5.7 with potassium carbonate or glacial acetic acid |
| Stabilizing solution | | |
| 5-Chloro-2-methyl-4-isothiazolin-3-one | | 1 g |
| 1-Hydroxyethylidene-1,1-diphosphonic acid | | 2 g |
| Water | | to make 1,000 ml |
| pH | | adjusted to 7.0 with $H_2SO_4$ or KOH |

TABLE 6

| Sample | Coupler | Maximum density (Dmax) | Light-fastness (%) |
|---|---|---|---|
| 501 (comparison) | Y-7 | 2.35 | 65 |
| 502 (invention) | exemplary compound (50) | 2.45 | 84 |
| 503 (invention) | exemplary compound (63) | 2.40 | 83 |
| 504 (invention) | exemplary compound (65) | 2.42 | 85 |

As is clear from Table 6, the compounds of the present invention provided satisfactory level of color density even when their coupler residues did not take part in image formation. In addition, the resulting dye images were excellent in lightfastness.

In summary, the present invention successfully provided silver halide photographic materials containing novel colorless couplers that were capable of efficient dye formation.

What is claimed is:

1. A silver halide photographic material comprising a substantially colorless coupler, wherein said coupler has a leaving group with a protected formyl group at the active site, said protected formyl group being such that subsequent to the elimination of the leaving group upon coupling reaction, the protective group for a formyl group undergoes cleavage, causing reaction with an aromatic primary amine to form a non-diffusible Schiff type dye.

2. The silver halide photographic material of claim 1 wherein said coupler is a compound represented by the following general formula (I):

$$Cp-(L)_n-A \qquad (I)$$

where Cp is a coupler residue excluding the hydrogen atom at the active site; L is a linkage group; n is 0 or 1; and A is an organic group having a protected formyl group.

3. The silver halide photographic material of claim 2 wherein the coupler residue represented by Cp is a yellow coupler residue selected from among benzoyl acetanilides and pivaloyl acetanilides.

4. The silver halide photographic material of claim 2 wherein the coupler residue represented by Cp is a magenta coupler residue selected from among pyrazolones and pyrazoloazoles.

5. The silver halide photographic material of claim 2 wherein the coupler residue represented by Cp is a cyan coupler selected from among phenols and naphthols.

6. The silver halide photographic material of claim 2 wherein the coupler residue represented by Cp is a coupler residue that forms a colorless product and that is selected from among cyclic carbonyl compounds.

7. The silver halide photographic material of claim 2 wherein the linkage group represented by L is more specifically represented by the following general formula (II), (III) or (IV):

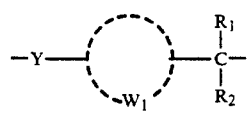

(II)

where $W_1$ is the atomic group necessary to form an optionally substituted benzene or naphthalene ring; Y is —O—, —S— or —N($R_3$) and is bound at the coupling site to the coupler residue represented by Cp in the general formula (I); $R_1$, $R_2$ and $R_3$ are each a hydrogen atom, an alkyl group or an aryl group; and —C($R_1$)($R_2$)— which is substituted in the position ortho or para to Y is bound to A;

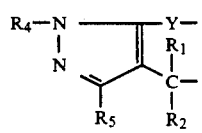

(III)

where Y, $R_1$ and $R_2$ respectively have the same meanings as defined for Y, $R_1$ and $R_2$ in the general formula (II); $R_4$ is a hydrogen atom, an alkyl group, an aryl group, an acyl group, a sulfonyl group, an alkoxycarbonyl group or a heterocyclic residue; $R_5$ is a hydrogen atom, an alkyl group, an aryl group, a heterocyclic residue, an alkoxy group, an amino group, an acid amido group, a sulfonamido group, a carboxyl group, an alkoxycarbonyl group, a carbamoyl group or a cyano group; as in the general formula (II), the linkage group of the general formula (III) is bound via Y to the coupling site of the coupler residue represented by Cp in the general formula (I) and is bound to A via —C($R_1$)($R_2$)—;

$$-Nu-Z-E- \qquad (IV)$$

where Nu is a nucleophilic group having an oxygen, sulfur or nitrogen atom and it is bound at the coupling site to the coupler residue represented by Cp in the general formula (I); E is an electrophilic group having a carbonyl, thiocarbonyl, phosphinyl or thiophosphinyl group and it is bound to A; Z is a bonding group that sterically relates Nu and E and which, after Nu is released from the coupler residue represented by Cp in the general formula (I), undergoes an intramolecular nucleophilic reaction involving the formation of a 3- to 7-membered ring to thereby release A.

8. The silver halide photographic material of claim 2 wherein the organic group having a protected formyl group and which is represented by A is more specifically represented by the following general formula (V), (VI) or (VII):

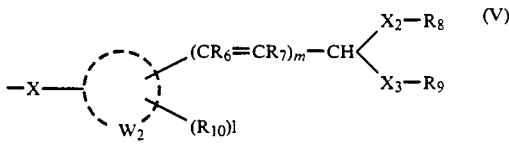

where m is an integer of 0–2; $R_6$ and $R_7$ each independently represents a hydrogen atom or a substituent; $R_8$ and $R_9$ each represents an alkyl group, an aryl group, an alkylsulfonyl group, an arylsulfonyl group or an acyl group, provided that $R_8$ and $R_9$ may combine together to form a cyclic structure; $R_{10}$ represents a straight or branched alkyl group having 1–30 carbon atoms, a halogen atom, an aryl group, an alkoxy group, an aryloxy group, an alkylthio group, an arylthio group, a carbamoyl group, a sulfamoyl group, an acylamino group, a sulfonylamino group, an alkyloxycarbamoyl group, a nitro group, a cyano group, a hydroxyl group, an amino group, an alkylamino group or an arylamino group; l is an integer of 1–4; at least one of $R_6$, $R_7$ and $R_{10}$ has a group with 10–40 carbon atoms; X, $X_2$ and $X_3$ each represents an oxygen atom, a sulfur atom or a divalent bonding group $NR_{11}$, where $R_{11}$ is an alkyl group, an aryl group, an alkylsulfonyl group, an arylsulfonyl group, an acyl group or an acylamino group; $W_2$ represents a group capable of forming a 5- or 6-membered aromatic or heteroaromatic ring;

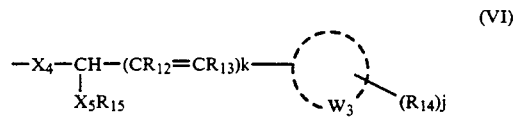

where k is an integer of 0–2; $R_{12}$ and $R_{13}$ each independently represents a hydrogen atom or a substituent; $R_{14}$ has the same meaning as defined for $R_{10}$ in the general formula (V); j is an integer of 1–5; at least one of $R_{12}$, $R_{13}$ and $R_{14}$ has a group with 10–40 carbon atoms; $R_{15}$ is an alkyl group, an aryl group, an alkylsulfonyl group or an arylsulfonyl group; $X_4$ and $X_5$ each represents an oxygen atom, a sulfur atom or a divalent bonding group $NR_{16}$, where $R_{16}$ is an alkyl group, an aryl group, an alkylsulfonyl group, an arylsulfonyl group, an acyl group or an acylamino group; and $W_3$ has the same meaning as defined for $W_2$ in the general formula (V);

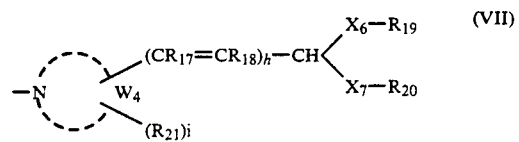

where $R_{17}$ and $R_{18}$ respectively have the same meanings as defined for $R_6$ and $R_7$ in the general formula (V); $R_{19}$ and $R_{20}$ respectively have the same meanings as defined for $R_8$ and $R_9$ in the general formula (V); $R_{21}$ has the same meaning as defined for $R_{10}$ in the general formula (V); h is an integer of 0–2; i is an integer of 0–4; $W_4$ is a group capable of forming a 5- or 6-membered hetero ring; and $X_6$ and $X_7$ each represents an oxygen atom, a sulfur atom or a divalent bonding group $NR_{22}$, where $R_{22}$ is an alkyl group, an aryl group, an alkylsulfonyl group, an arylsulfonyl group, an acyl group or an acylamino group.

9. The silver halide photographic material of claim 8 wherein the organic group with a protected formyl group which is represented by A is a compound represented by the general formula (V), in which $X_2$ and $X_3$ are each an oxygen atom, or one of them is an oxygen atom while the other is a sulfur atom, or they are each a sulfur atom.

10. The silver halide photographic material of claim 1 wherein said coupler is contained in an amount of $2 \times 10^{-5}$ to $1 \times 10^{-3}$ mole per square meter of the layer in which it is incorporated.

* * * * *

UNITED STATES PATENT AND TRADEMARK OFFICE
CERTIFICATE OF CORRECTION

PATENT NO. : 5,169,749
DATED : December 08, 1992
INVENTOR(S) : Eisaku Katoh et al.

It is certified that error appears in the above-identified patent and that said Letters Patent is hereby corrected as shown below:

Claim 8, column 84, line 19, change "bouding" to --bonding--.

Signed and Sealed this

Fourth Day of January, 1994

Attest:

BRUCE LEHMAN

Attesting Officer

Commissioner of Patents and Trademarks